(12) United States Patent
Clague et al.

(10) Patent No.: US 7,422,905 B2
(45) Date of Patent: *Sep. 9, 2008

(54) BLOOD COAGULATION TEST CARTRIDGE, SYSTEM, AND METHOD

(75) Inventors: Cynthia T. Clague, Minnetonka, MN (US); Daniel S. Cheek, Plymouth, MN (US); Douglas D. Nippoldt, Oakdale, MN (US)

(73) Assignee: Medtronic, Inc., Minneapolis, MN (US)

( * ) Notice: Subject to any disclaimer, the term of this patent is extended or adjusted under 35 U.S.C. 154(b) by 577 days.

This patent is subject to a terminal disclaimer.

(21) Appl. No.: 10/826,994

(22) Filed: Apr. 19, 2004

(65) Prior Publication Data

US 2005/0233460 A1 Oct. 20, 2005

(51) Int. Cl.
*G01N 33/86* (2006.01)

(52) U.S. Cl. .................... 436/69; 436/45; 436/63; 422/72; 422/73; 422/99; 435/13; 600/369; 73/64.41

(58) Field of Classification Search ............... 436/43, 436/45, 63, 69, 149, 150; 422/72, 73, 99, 422/102; 435/2, 13; 600/368, 369; 73/64.41, 73/64.43
See application file for complete search history.

(56) References Cited

U.S. PATENT DOCUMENTS

| | | | |
|---|---|---|---|
| 3,053,078 A | 9/1962 | Jewett | |
| 3,695,842 A | 10/1972 | Mintz | |
| 3,766,774 A | 10/1973 | Clark | |
| 4,000,972 A | 1/1977 | Braun et al. | |
| 4,074,971 A | 2/1978 | Braun et al. | |
| 4,244,919 A | 1/1981 | Chen | |
| 4,533,519 A | 8/1985 | Baugh et al. | |
| 4,534,939 A | 8/1985 | Smith et al. | |
| 4,599,219 A | 7/1986 | Cooper et al. | |

(Continued)

FOREIGN PATENT DOCUMENTS

EP 1 503 211 2/2005

(Continued)

OTHER PUBLICATIONS

PCT International Search Report from International Application No. PCT/US2005/011775, dated Jul. 29, 2005.

(Continued)

*Primary Examiner*—Maureen M Wallenhorst
(74) *Attorney, Agent, or Firm*—Mike Jaro; Jeffrey J. Hohenshell

(57) ABSTRACT

A system and method for determining a coagulation time, e.g., TT, PT, aPTT, and ACT, of a test sample deposited in a test cartridge is disclosed. A cartridge housing having upper and lower major sides and a minor sidewall encloses a test chamber having a test chamber pivot element and is provided with a cartridge port for introducing a test sample into the test chamber. Ferromagnetic agitator vane leaflets extend from an agitator pivot element supported by the test chamber pivot element intermediate the upper and lower major sides for rotational motion. The agitator vane leaflets can be swept, in response to an external magnetic field, through the test sample in the absence of coagulation. A timer is started when the agitator movement is commenced whereupon the agitator moves freely. Resistance to agitator movement due to coagulation is detected, and the coagulation time is measured.

18 Claims, 14 Drawing Sheets

U.S. PATENT DOCUMENTS

| | | |
|---|---|---|
| 4,604,894 A | 8/1986 | Kratzer et al. |
| 4,659,550 A | 4/1987 | Schildknecht |
| 4,662,127 A | 5/1987 | Glode |
| 4,725,554 A | 2/1988 | Schildknecht |
| 4,752,449 A | 6/1988 | Jackson et al. |
| 4,774,057 A | 9/1988 | Uffenheimer et al. |
| 4,780,418 A | 10/1988 | Kratzer |
| 4,782,026 A | 11/1988 | Baugh et al. |
| 4,788,139 A | 11/1988 | Ryan |
| 4,849,340 A | 7/1989 | Oberhardt |
| 4,871,677 A | 10/1989 | Baugh et al. |
| 4,952,372 A | 8/1990 | Huber |
| 4,954,087 A | 9/1990 | Lauks et al. |
| 4,964,728 A | 10/1990 | Kloth et al. |
| 5,039,617 A | 8/1991 | McDonald et al. |
| 5,051,239 A | 9/1991 | von der Goltz |
| 5,089,422 A | 2/1992 | Brubaker |
| 5,104,808 A | 4/1992 | Laska et al. |
| 5,110,727 A | 5/1992 | Oberhardt |
| 5,124,661 A | 6/1992 | Zelin et al. |
| 5,171,538 A | 12/1992 | Tremmel et al. |
| 5,174,961 A | 12/1992 | Smith |
| 5,184,188 A | 2/1993 | Bull et al. |
| 5,248,616 A | 9/1993 | Beckman et al. |
| 5,266,462 A | 11/1993 | Hemker et al. |
| 5,296,379 A | 3/1994 | Gorog et al. |
| 5,300,779 A | 4/1994 | Hillman et al. |
| 5,302,348 A | 4/1994 | Cusack et al. |
| 5,314,826 A | 5/1994 | Baugh |
| 5,316,730 A | 5/1994 | Blake et al. |
| 5,325,295 A | 6/1994 | Fratantoni et al. |
| 5,339,375 A | 8/1994 | Kerns |
| 5,339,830 A | 8/1994 | Blake, III |
| 5,344,754 A | 9/1994 | Zweig |
| 5,350,676 A | 9/1994 | Oberhardt et al. |
| 5,372,946 A | 12/1994 | Cusak et al. |
| 5,399,497 A | 3/1995 | Kumar et al. |
| 5,418,141 A | 5/1995 | Zweig et al. |
| 5,418,143 A | 5/1995 | Zweig et al. |
| 5,425,921 A | 6/1995 | Coakley et al. |
| 5,432,084 A | 7/1995 | Brubaker |
| 5,441,892 A | 8/1995 | Baugh |
| 5,447,691 A | 9/1995 | Sanuki |
| 5,504,011 A | 4/1996 | Gavin et al. |
| 5,508,521 A | 4/1996 | Kraft et al. |
| 5,523,238 A | 6/1996 | Varon et al. |
| 5,526,111 A | 6/1996 | Collins et al. |
| 5,534,226 A | 7/1996 | Gavin et al. |
| 5,534,336 A | 7/1996 | Nomura et al. |
| 5,540,081 A | 7/1996 | Takeda et al. |
| 5,547,850 A | 8/1996 | Nowak et al. |
| 5,554,531 A | 9/1996 | Zweig |
| 5,558,838 A | 9/1996 | Uffenheimer |
| 5,561,069 A | 10/1996 | Brigham-Burke et al. |
| 5,580,744 A | 12/1996 | Zweig |
| 5,591,403 A | 1/1997 | Gavin et al. |
| 5,599,718 A | 2/1997 | Gorog |
| 5,601,991 A | 2/1997 | Oberhardt |
| 5,602,037 A | 2/1997 | Ostgaard et al. |
| 5,612,187 A | 3/1997 | Brubaker |
| 5,628,961 A | 5/1997 | Davis et al. |
| 5,629,209 A * | 5/1997 | Braun et al. ............... 436/69 |
| 5,646,046 A | 7/1997 | Fischer et al. |
| 5,665,311 A | 9/1997 | Gorog et al. |
| 5,695,720 A | 12/1997 | Wade et al. |
| 5,716,796 A | 2/1998 | Bull et al. |
| 5,731,212 A | 3/1998 | Gavin et al. |
| 5,736,404 A | 4/1998 | Yassinzadeh et al. |
| 5,755,939 A | 5/1998 | Dror et al. |
| 5,789,664 A | 8/1998 | Neel et al. |
| 5,800,781 A | 9/1998 | Gavin et al. |
| 5,807,471 A | 9/1998 | Dror et al. |
| 5,821,399 A | 10/1998 | Zelin |
| 5,837,203 A | 11/1998 | Godec et al. |
| 5,849,592 A | 12/1998 | Pollema et al. |
| 5,854,076 A | 12/1998 | Kundu et al. |
| 5,854,423 A | 12/1998 | Venegas |
| 5,864,017 A | 1/1999 | Brubaker |
| 5,865,749 A | 2/1999 | Doten et al. |
| 5,888,826 A | 3/1999 | Ostgaard et al. |
| 5,916,813 A | 6/1999 | Gorog |
| 5,922,551 A | 7/1999 | Durbin et al. |
| 5,925,319 A | 7/1999 | Baugh et al. |
| 5,925,569 A | 7/1999 | Gorog et al. |
| 5,951,951 A | 9/1999 | Lane et al. |
| 5,958,716 A | 9/1999 | Kundu |
| 5,972,712 A | 10/1999 | Baugh et al. |
| 6,004,819 A | 12/1999 | Gorog et al. |
| 6,010,911 A | 1/2000 | Baugh et al. |
| 6,016,193 A | 1/2000 | Freeman et al. |
| 6,016,712 A | 1/2000 | Warden et al. |
| 6,033,628 A | 3/2000 | Kaltenbach et al. |
| 6,040,186 A | 3/2000 | Lewis et al. |
| 6,043,871 A | 3/2000 | Solen et al. |
| 6,046,051 A | 4/2000 | Jina |
| 6,054,326 A | 4/2000 | Dubus |
| 6,060,323 A | 5/2000 | Jina |
| 6,061,128 A | 5/2000 | Zweig et al. |
| 6,066,504 A | 5/2000 | Jina |
| 6,077,233 A | 6/2000 | Blake, III |
| 6,101,449 A | 8/2000 | Givens et al. |
| 6,144,444 A | 11/2000 | Haworth et al. |
| 6,149,872 A | 11/2000 | Mack et al. |
| 6,159,741 A | 12/2000 | Kratzer et al. |
| 6,189,370 B1 | 2/2001 | Neel et al. |
| 6,190,614 B1 | 2/2001 | Fukunaga |
| 6,197,494 B1 | 3/2001 | Oberhardt |
| 6,200,532 B1 | 3/2001 | Wu et al. |
| 6,221,672 B1 | 4/2001 | Baugh et al. |
| 6,232,127 B1 | 5/2001 | Lane et al. |
| 6,245,573 B1 | 6/2001 | Spillert |
| 6,315,952 B1 | 11/2001 | Sklar et al. |
| 6,338,821 B1 | 1/2002 | Jina |
| 6,344,172 B1 | 2/2002 | Afeyan et al. |
| 6,365,107 B1 | 4/2002 | Markelov et al. |
| 6,391,568 B1 | 5/2002 | Schneider et al. |
| 6,410,337 B1 | 6/2002 | Brady et al. |
| 6,416,718 B1 | 7/2002 | Maiefski et al. |
| 6,438,498 B1 | 8/2002 | Opalsky et al. |
| 6,448,024 B1 | 9/2002 | Bruegger |
| 6,451,610 B1 | 9/2002 | Gorman et al. |
| 6,472,161 B1 | 10/2002 | Baugh |
| 6,488,897 B2 | 12/2002 | Dubrow et al. |
| 6,495,104 B1 | 12/2002 | Unno et al. |
| 6,527,744 B1 | 3/2003 | Kriesel et al. |
| 6,531,095 B2 | 3/2003 | Hammer et al. |
| 6,541,262 B1 | 4/2003 | Baugh et al. |
| 6,555,064 B2 | 4/2003 | Baugh et al. |
| 6,555,066 B2 | 4/2003 | Baugh et al. |
| 6,555,381 B2 | 4/2003 | Baugh et al. |
| 6,573,104 B2 | 6/2003 | Carr, Jr. et al. |
| 6,575,017 B1 | 6/2003 | Neel et al. |
| 6,586,259 B1 | 7/2003 | Mahan et al. |
| 6,613,573 B1 | 9/2003 | Cohen |
| 6,620,310 B1 | 9/2003 | Ohara et al. |
| 6,629,057 B2 | 9/2003 | Zweig et al. |
| 6,632,678 B2 | 10/2003 | Aiken et al. |
| 6,645,768 B1 | 11/2003 | Tejidor et al. |
| 6,676,902 B2 | 1/2004 | Baugh et al. |
| 6,680,177 B2 | 1/2004 | Mize |
| 6,692,969 B1 | 2/2004 | Berg et al. |
| 6,733,471 B1 | 5/2004 | Ericson et al. |
| 6,750,053 B1 | 6/2004 | Widrig Opalsky et al. |
| 6,761,856 B2 | 7/2004 | Baugh et al. |

| | | |
|---|---|---|
| 6,790,632 B2 | 9/2004 | Zweig |
| 6,887,429 B1 | 5/2005 | Marshall et al. |
| 2001/0021355 A1 | 9/2001 | Baugh et al. |
| 2001/0053337 A1 | 12/2001 | Doktycz et al. |
| 2002/0028517 A1 | 3/2002 | Brady et al. |
| 2002/0049557 A1 | 4/2002 | Chen |
| 2002/0081741 A1 | 6/2002 | Braun, Sr. et al. |
| 2003/0027235 A1 | 2/2003 | Kraus et al. |
| 2003/0150745 A1 | 8/2003 | Teodorczyk et al. |
| 2003/0156989 A1 | 8/2003 | Safir et al. |
| 2003/0180824 A1* | 9/2003 | Mpock et al. ............. 435/13 |
| 2003/0211551 A1 | 11/2003 | Mahan et al. |
| 2004/0011672 A1 | 1/2004 | Ohara et al. |
| 2004/0019300 A1 | 1/2004 | Leonard |
| 2004/0043499 A1 | 3/2004 | Lee-Alvarez |
| 2004/0156045 A1 | 8/2004 | Zweig et al. |
| 2004/0166590 A1 | 8/2004 | Green |
| 2004/0224416 A1 | 11/2004 | Ghai et al. |
| 2005/0006237 A1 | 1/2005 | Larkin |
| 2005/0196748 A1 | 9/2005 | Ericson |
| 2005/0255601 A1 | 11/2005 | Nippoldt et al. |

FOREIGN PATENT DOCUMENTS

| | | |
|---|---|---|
| SU | 1130306 | * 12/1984 |
| WO | 02/063273 | 8/2002 |
| WO | 03/087817 | 10/2003 |

OTHER PUBLICATIONS

Flom-Halverson et al., "Assessment of Heparin Anticoagulation: Comparison of Two Commercially Available Methods," Ann. Thorac. Surg. 1999:67:1012-1016.

U.S. Appl. No. 10/892,000 non-final office action mailed Apr. 2, 2007, 14 pgs.

U.S. Appl. No. 10/892,000 final office action mailed Oct. 30, 2007, 7 pgs.

* cited by examiner

50

50

FIG. 7
<u>80, 100</u>
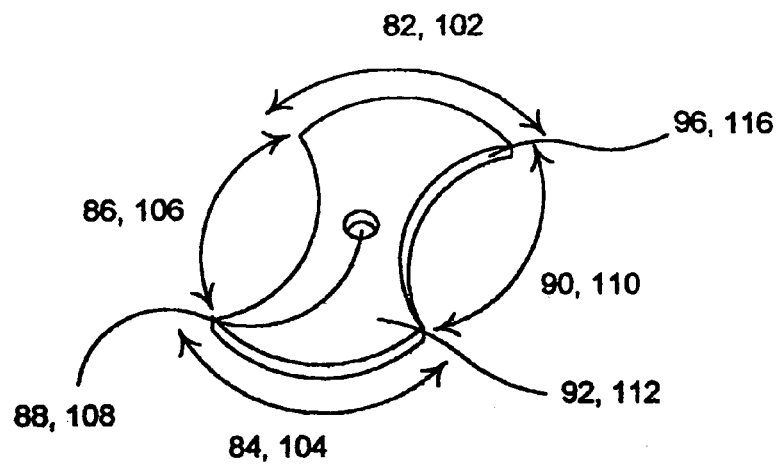
FIG. 8
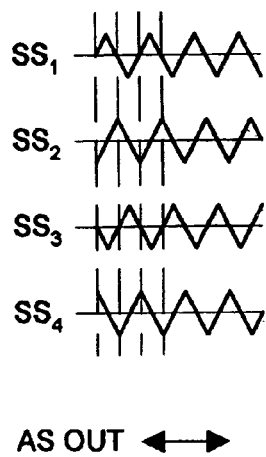
AS OUT ←→
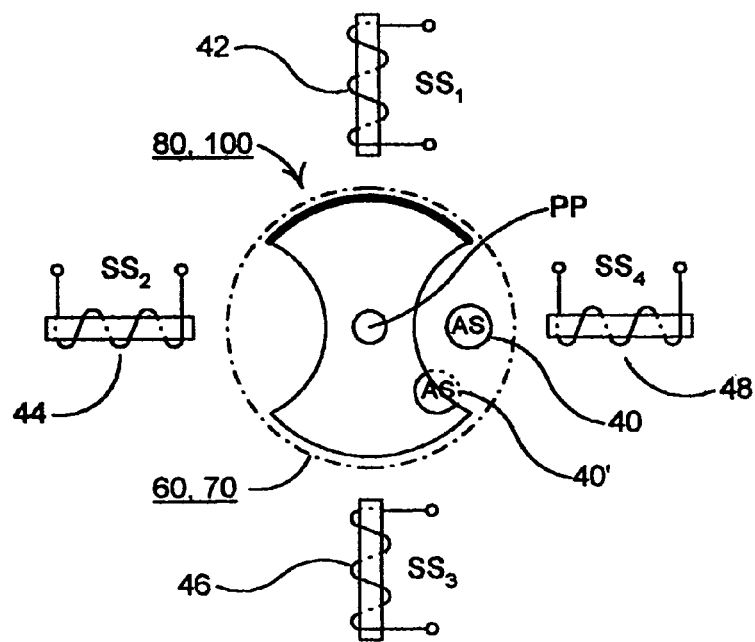

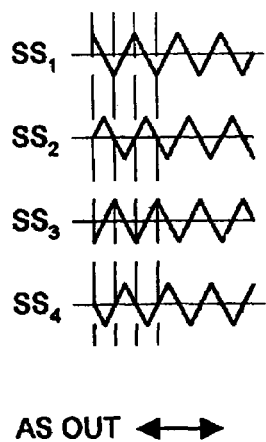
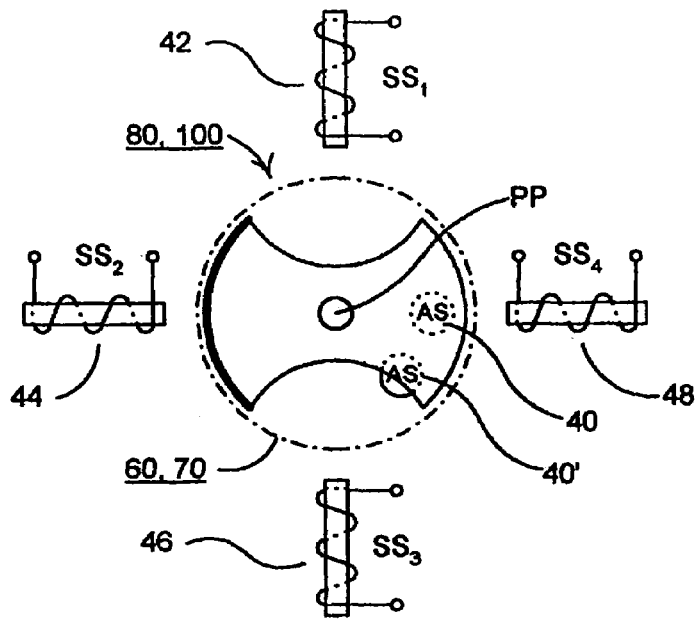
FIG. 9
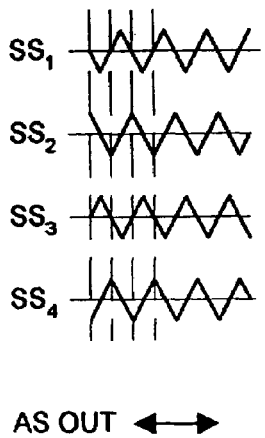
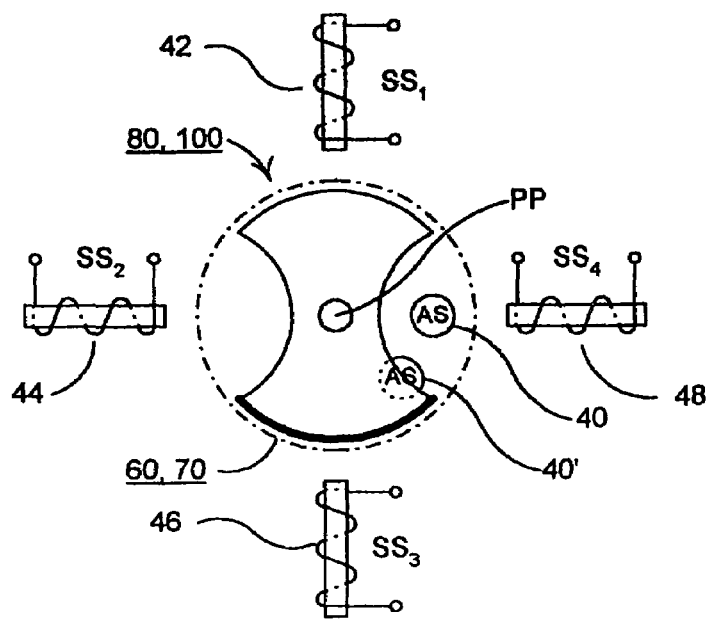
FIG. 10

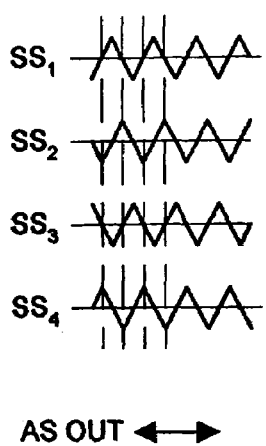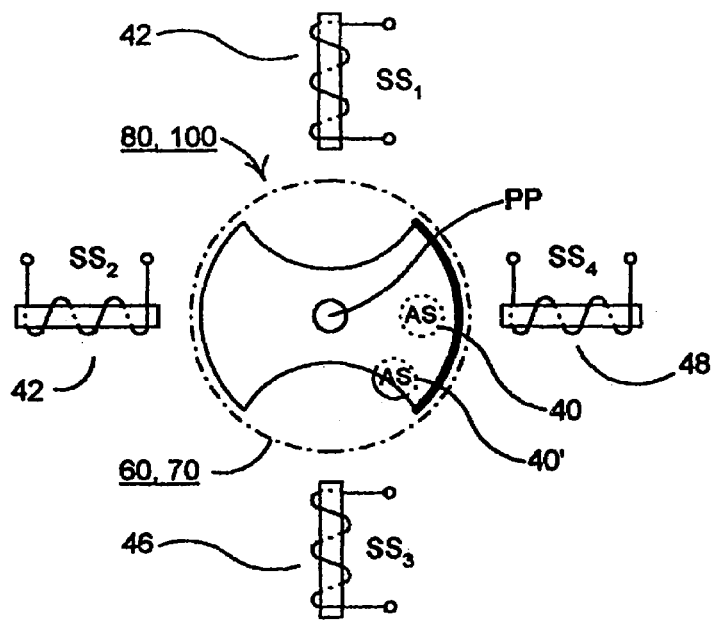
FIG. 11
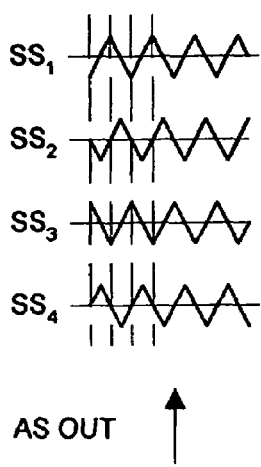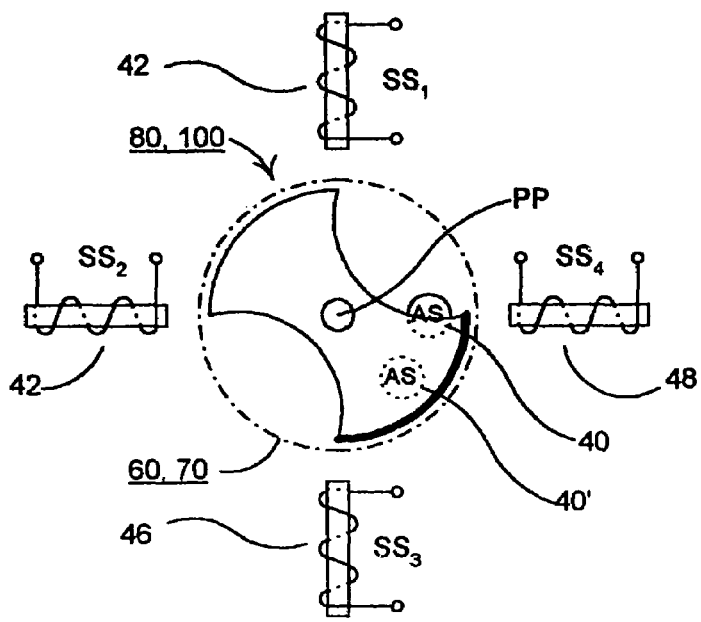
FIG. 12

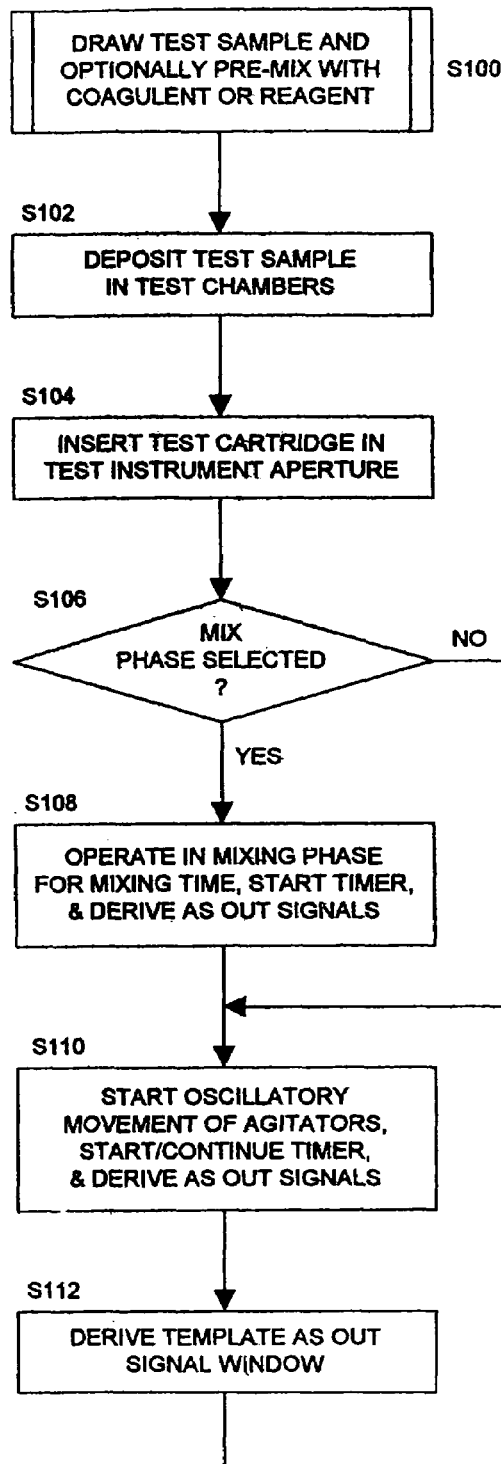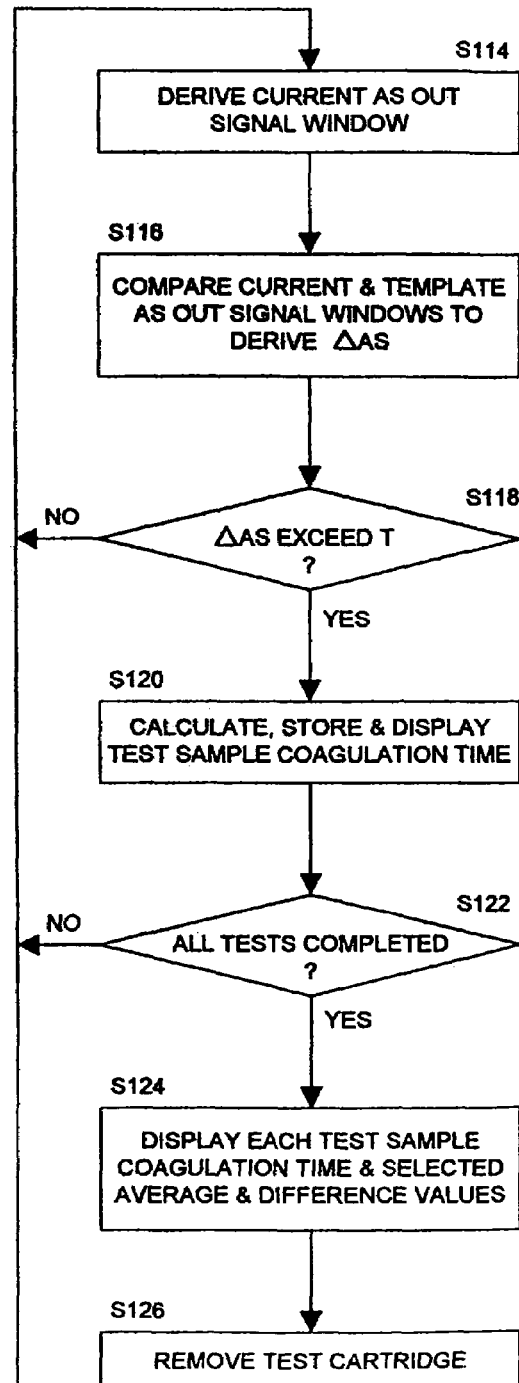
FIG. 14

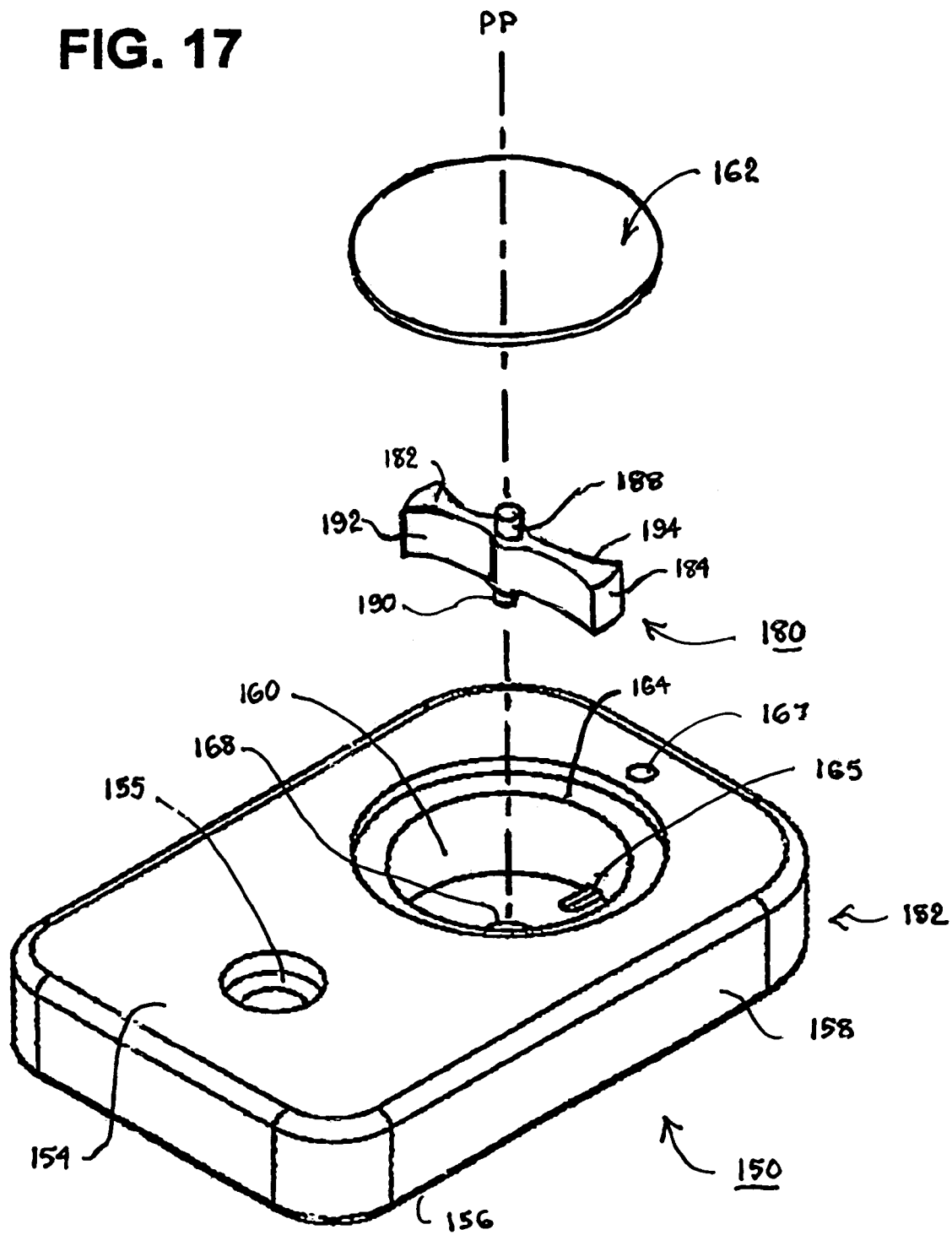

BLOOD COAGULATION TEST CARTRIDGE, SYSTEM, AND METHOD

REFERENCE TO RELATED APPLICATION

Reference is hereby made to commonly assigned U.S. Provisional Application No. 60/653,320 filed on Apr. 19, 2004 and U.S. application Ser. No. 10/892,000 filed Jul. 15, 2004 for BLOOD COAGULATION TEST CARTRIDGE, SYSTEM, AND METHOD in the name of David Wright et al.

FIELD OF THE INVENTION

This invention relates to detecting changes in viscosity of biologic fluid test samples, e.g., detecting coagulation and coagulation-related activities including agglutination and fibrinolysis of human blood test samples, and more particularly to improved methods and apparatus for obtaining a coagulation time of a blood test sample.

BACKGROUND OF THE INVENTION

Blood coagulation is a complex chemical and physical reaction that occurs when blood (herein, "blood" shall mean whole blood, citrated blood, platelet concentrate, plasma, or control mixtures of plasma and blood cells, unless otherwise specifically called out) comes into contact with an activating agent, such as an activating surface or an activating agent. In accordance with one simplified conceptual view, the whole blood coagulation process can be generally viewed as three activities: platelet adhesion, platelet aggregation, and formation of a fibrin clot. In vivo, platelets flow through the blood vessels in an inactivated state because the blood vessel lining, the endothelium, prevents activation of platelets. When a blood vessel is damaged, however, the endothelium loses its integrity and platelets are activated by contact with tissue underlying the damaged site. Activation of the platelets causes them to become "sticky" and adhere together. Additional platelets then adhere to the activated platelets and also become activated. This process continues until a platelet "plug" is formed. This platelet plug then serves as a matrix upon which blood clotting or coagulation proceeds. Blood "coagulation" and "clotting" are used interchangeably herein unless specifically distinguished from one another.

If the chemical balance of the blood is suitable, thrombin is then produced that causes fibrinogen to convert to fibrin, which forms the major portion of the clot mass. During clotting, additional platelets are activated and trapped in the forming clot, contributing to clot formation. As clotting proceeds, polymerization and cross-linking of fibrin results in the permanent clot. Thus, platelet activation plays a very important function in blood coagulation.

The clinical assessment of clotting function has long been recognized to be important in the management of surgical patients. Preoperatively, the assessment of the clotting function of the patient's blood is utilized as a predictor of risk of patient bleeding, allowing advanced preparation of blood components. Perioperative monitoring of the clotting function of the patient's blood is also important because coagulopathies can be induced by hemodilution of procoagulants, fibrinogen and platelets, by consumption of coagulation factors during surgical procedures, or by cardiopulmonary bypass. Post-operative assessment of clotting function is also crucial to the patient's successful recovery. For example, 3-5% of cardiopulmonary bypass patients require surgical reoperation to stop bleeding. Prompt assessment of clotting function could rule out coagulopathy as the cause of bleeding and could avoid unnecessary surgery that adds to patient morbidity and treatment costs.

Several tests of coagulation are routinely utilized to assess the complicated cascade of events leading to blood clot formation and test for the presence of abnormalities or inhibitors of this process. Among these tests are platelet count (PLT), thrombin time (TT), prothrombin time (PT), partial thromboplastin time (aPTT), activated clotting time (ACT), fibrinogen level (FIB), fibrinogen degradation product concentrations, and general purpose clotting (GPC) time. The aPTT test can be used to assess the degree of anticoagulation resulting from heparin administration. The PT test results can indicate the level of anticoagulation produced by warfarin (coumadin) administration. In the GPC test, the blood sample is exposed to calcium as an activating agent, but other reagents can be added to conduct the aPTT test, for example.

The ACT tests are further differentiated into high range ACT (HRACT), low rate ACT (LRACT), recalcified ACT (RACT), and HRHTC tests. The HRACT test features a slope response to moderate to high heparin levels in whole blood drawn from a patient during cardiac surgery for use in whole blood coagulation time tests. The LRACT test features a more sensitive slope response to heparin levels ideal for use in whole blood coagulation time tests run in the ICU, CCU and during dialysis. The RACT test is similar to the LRACT test, but the test is conducted on a citrated blood test sample, rather than a whole blood sample, and is typically conducted at a central testing station remote from the patient the test sample is drawn from.

The HRHTC test is a variation upon the HRACT test where an enzyme, heparinase, is added as a deactivating or neutralizing reagent to one test sample of the whole blood drawn from the patient to neutralize any heparin therein and thereby provide a heparin-free blood test sample. In this test, comparative coagulation times are determined from the heparinase-exposed blood test sample and the unexposed blood test sample. The two ACT test times will be close if no heparin is present in the whole blood drawn from the patient. The ACT test conducted on the heparinase-exposed blood test sample will result in a shorter coagulation test time than the ACT test conducted on the unexposed blood test sample, thereby establishing that the patient's blood contains at least some level of heparin.

During heart bypass surgery, the platelets of blood circulated in an extracorporeal circuit may become activated by contact with the materials present in the extracorporeal circuit. This activation may be reversible or irreversible. Once platelets are irreversibly activated, they lose their ability to function further. A deficiency of functional platelets in the blood may be indicative of an increased probability of a post-operative bleeding problem. Such a deficiency, and the resulting post-operative bleeding risk, could be remedied by a transfusion of platelet concentrate. Platelet functionality tests, e.g., the ACT test, can identify a deficiency of platelets or functional platelets and aid the attending surgeon in ascertaining when to administer a platelet concentrate transfusion. Such a test is further useful in ascertaining the efficacy of a platelet transfusion. By performing the platelet functionality test following a platelet transfusion, it is possible to determine if additional platelet concentrate transfusions are indicated. Real-time assessment of clotting function at the operative site is preferred to evaluate the result of therapeutic interventions and also to test and optimize, a priori, the treatment choice and dosage.

A number of different medical apparatus and testing methods have been developed for measuring and determining platelet activation and coagulation-related conditions of blood that can be used in real time during surgery, particularly bypass surgery, on fresh drawn blood samples or that can be used after some delay on citrated blood samples. Some of the more successful techniques of evaluating blood clotting and coagulation of fresh or citrated blood samples employ plunger techniques disclosed in commonly assigned U.S. Pat. Nos. 4,599,219, 4,752,449, 5,174,961, 5,314,826, 5,925,319, and 6,232,127, for example. These techniques are embodied in the ACT II® automatic coagulation timer, commercially sold by the assignee of this patent application.

In U.S. Pat. No. 5,302,348, an apparatus and method are disclosed for performing a coagulation time test on a sample of blood deposited in a fluid reservoir of a disposable cuvette. A capillary conduit having at least one restricted region is formed within the cuvette. The cuvette is inserted into a testing machine that engages the cuvette and draws blood from the fluid reservoir into the capillary conduit. The blood is then caused to reciprocally move back and forth within the capillary conduit so that the blood is forced to traverse the restricted region. Optical sensors of the testing machine are employed to detect movement of the blood. The testing machine measures the time required each time the blood is caused to traverse the restricted region. Coagulation is considered to have occurred and the overall coagulation time is displayed to the operator when a measured time is a predetermined percentage longer than an immediately preceding time.

In U.S. Pat. No. 5,504,011, a similar apparatus and method are disclosed for performing multiple coagulation time tests on a sample of blood deposited in a fluid reservoir of a disposable cuvette having multiple capillary conduits within the cuvette. Each of the conduits contains a dried or lyophilized activation reagent that is rehydrated by the blood. The blood in each conduit is then reciprocally moved across a restricted region of the conduit until a predetermined degree of coagulation occurs. Since the coagulation time is being monitored in multiple conduits, a representation coagulation time for a given sample can be determined. A normalizing control agent is present in at least one of the conduits. The normalizing control agent counteracts any effects of anticoagulants present in the blood sample, thereby allowing the blood sample to have generally normal coagulation characteristics. The normalized blood is tested simultaneously with the untreated blood to provide a reference value against which the functionality of the test system and the quality of the sample can be judged.

The apparatus and methods disclosed in the '348 and '011 patents only check the state of the sample during the reciprocal back and forth movement of the sample through the restricted region capillary. The detection of coagulation would be delayed or inaccurate if the sample coagulates between movement cycles.

In U.S. Pat. No. 6,200,532, a device and method for performing blood coagulation assays, particularly prothrombin times and activated partial thromboplastin times and other clotting parameters are disclosed. One embodiment of the device comprises a disposable cassette containing a sample inlet for sample delivery, a pair of interleaved spiral capillary channels for driving force, and a reaction chamber with an appropriate dry reagent for a specific assay, and a piezoelectric sensor. The device could also include a heating element for temperature control, and a magnetic bender. Compressed air is employed to drive the sample into the two spiral capillary channels. The magnetic bender is driven by an electromagnetic field generator and is attached onto a piezoelectric film in contact with the blood sample. The electric signal generated in the piezoelectric film is characterized by its frequency and amplitude due to the movement of the attached metal film. The signal collected at the site of the piezoelectric film represents the process of a biochemical reaction in the reaction chamber as the blood sample proceeds to the point at which clot formation starts and is amplified by an amplifier and rectified into a DC voltage and is sent to a recording unit and/or display unit.

A method and apparatus for measuring coagulation of blood is disclosed in U.S. Pat. No. 4,879,432, wherein a timer is started as a stream of solid particles are introduced into a tube containing the blood sample that descend through the blood sample under the force of gravity. The particles are micron-sized grains of glass, for example, that are highly wettable and can descend through the blood sample until stopped by the fibrin network that forms as coagulation begins. Photoelectric cells detect the stopping of the particles, and the coagulation time is determined.

Other approaches to the detection of a change in viscosity of a fluid, particularly changes accompanying fibrin formation and clotting in blood samples, have been disclosed involving ferromagnetic elements or materials introduced in the fluid that are inhibited from moving freely when the viscosity change or clotting occurs.

For example, a method and apparatus is disclosed in U.S. Pat. No. Re. 27, 866 wherein the coagulation of a blood plasma sample is intensified by dispersing iron oxide particles throughout the plasma sample. A rotating magnetic field is applied that causes the particles to move within the sample and activate the clotting reaction. The moving particles collect fibrin strands that are formed, thereby changing the optical properties of the particle-sample mixture, and the changed optical properties are detected optically.

Further methods and apparatus employing magnetic effects for determining changes in viscosity of a fluid, particularly a blood sample, within a test tube are disclosed in U.S. Pat. Nos. 3,635,678, 3,836,333, 3,967,934, and 5,145,082. In the '678 and '934 patents, a steel ball within the fluid is maintained at a certain location in the test tube by a magnetic field, while the tube is moved up and down. The magnetic force is insufficient to attract the ball when the fluid in the tube changes viscosity, and the failure of the steel ball to stay within the magnetic field is detected photoelectrically. In the '333 and '082 patents, a blood sample is placed in a test tube along with a ferromagnetic member. A magnetic field is applied to the ferromagnetic member, and the applied magnetic field maintains the ferromagnetic member oriented with the magnetic field as the test tube is rotated about its axis. The magnetic force is insufficient to attract the ball when the fluid in the tube changes viscosity, e.g., due to clotting, and the failure of the member to stay within the magnetic field is detected magnetically with a reed switch.

In other approaches to measuring coagulation time, a blood sample is disposed in a test chamber having a ferromagnetic element therein. The ferromagnetic element is raised against gravity, and the field is discontinued so that the ferromagnetic member drops through the sample in the test chamber.

For example, a viscometer is disclosed in U.S. Pat. No. 4,648,262 wherein the fluid sample under test is placed within a capillary tube along with a metal ball. A magnet mounted on a rotating drum periodically raises the ball to the top of the tube and then releases the ball so that it can fall to the bottom of the tube. The viscosity of the fluid is determined by the rate of descent of the ball in the tube.

Apparatus and methods for detecting changes in human blood viscosity are disclosed in U.S. Pat. Nos. 5,629,209 and 6,613,286, wherein heparinized blood is introduced into a test cartridge through an injection port and fills a blood receiving/ dispensing reservoir. The blood then moves from the reservoir through at least one conduit into at least one blood-receiving chamber where it is subjected to a viscosity test. A freely movable ferromagnetic washer is also located within the blood-receiving chamber that is moved up using an electromagnet of the test apparatus and allowed to drop with the force of gravity. Changes in the viscosity of the blood that the ferromagnetic washer falls through are detected by determining the position of the ferromagnetic washer in the blood-receiving chamber over a given time period or a given number of rises and falls of the ferromagnetic washer. The blood sample can be mixed with a viscosity-altering agent (e.g., protamine) as it passes through the conduit to the blood-receiving chamber. Air in the conduit and blood-receiving chamber is vented to atmosphere through a further vent conduit and an air vent/fluid plug as the blood sample is fills the blood-receiving chamber.

The movement of the washer in the above approach is actively controlled only when it is moved up, and the washer passively drops with the force of gravity. The washer is free to float in the test chamber and may drift side-to-side as it is moved up or floats downward. The side-to-side drifting movement may affect the rise time and the fall time, which could add error to the coagulation time measured. The washer may eventually stop moving as a clot forms about it, and no additional information can be obtained on the coagulation process in the sample.

It would be desirable to provide inexpensive, relatively simple, easy to use, and accurate equipment and techniques that quickly measure one or more of the aforementioned blood coagulation times, including TT, PT, aPTT, and ACT.

SUMMARY OF THE INVENTION

Therefore, the present invention provides a compact, inexpensive, disposable, test cartridge in which a test sample, particularly a blood or biologic test sample, to be tested is deposited and systems and methods for detecting a change in test sample viscosity. In a particular application, the present invention provides systems and methods for measuring a test coagulation time of such a test sample that are simple to practice, rapid, and reliable.

The test sample may comprise a biologic test sample or a blood test sample, e.g., whole blood drawn from a patient or plasma or blood concentrate or citrated blood, and the blood test sample can be maintained at body temperature, can be heparinized, and can be mixed with a reagent. The reagent is selected from coagulants or activating agents including calcium, kaolin, celite, ellagic acid, glass particles, thrombin, thromboplastin or other activating agents or from heparin neutralizing or deactivating agents including heparinase or protamine. The test coagulation time may comprise one or more of the aforementioned blood coagulation times, including TT, PT, aPTT, and ACT.

The test cartridge comprises a cartridge housing having at least one test chamber therein into which a test sample is deposited to be tested. An agitator vane of an agitator is mounted at a pivot point and is adapted to be swept about the pivot point and through the test sample in the test chamber when the test sample is not coagulated. A coagulation test time from the commencement of sweeping of the agitator vane until the detection of cessation or reduction of the sweeping movement is determinable.

In determining a coagulation time, a timer is started after a test sample is deposited in the test chamber and the agitator vane movement is commenced. The sweeping movement mixes the test sample, and the agitator vane initially sweeps through the test sample without encountering significant resistance. Resistance to agitator vane movement signifies coagulation of the test sample. The elapsed time measured from starting the sweeping movement and the detection of resistance constitutes a coagulation time.

The resistance to movement leads to a change or reduction in agitator vane movement, e.g., slowing agitator vane movement, reducing the range of the agitator vane movement or halting agitator vane movement. The reduction in agitator vane movement, including slowing of sweeping movement, reduction in range of movement, and absence or cessation of sweeping movement, is preferably detected by one or more agitator vane sensor and agitator movement detection circuitry coupled thereto. The agitator vane sensor may comprise one of a proximity sensor, inductive sensor, magnetic sensor, metal sensor, and optical sensor disposed at a sensor location with respect to the test chamber. Optionally, the detected movement of the agitator vane is displayed for observation of changes in agitator vane movement over time.

In a preferred embodiment, the test cartridge is formed of a cartridge housing having a substantially prismatic shape with upper and lower major sides and a minor sidewall extending between the upper and lower major sides and maintaining the upper and lower major sides in substantially parallel relation. Each test chamber extends between the upper and lower major sides in a portion of the cartridge housing thereby having a test chamber height. A test sample is deposited in a cartridge port and travels through a filling channel or capillary into the test chamber. Preferably, an air vent channel or capillary extends from the test chamber to an air vent.

In preferred embodiments, the agitator has an agitator pivot element engaging a test chamber pivot element defining the pivot point and a pivot axis, whereby the agitator vane extends from the agitator pivot element intermediate the upper and lower major sides and can be swept about the pivot axis at the pivot point in the absence of coagulation.

The agitator vane preferably comprises first and second agitator vane leaflets extending in opposed directions away from the agitator pivot element, the vane leaflets having a leaflet width, a leaflet thickness, and a leaflet length. The leaflet length is somewhat smaller than the test chamber radius, whereby the agitator vane leaflet extends from the agitator pivot element substantially across the test chamber radius. The vane leaflet height is somewhat smaller than the test chamber height, and the leaflet thickness is less than the vane leaflet height and the leaflet length. Thus, the preferred agitator vane shape possesses agitator leaflets that present enlarged agitator leaflet sweeping faces against the test sample disposed in the test chamber during rotation of the agitator vane leaflets.

The agitator vane leaflets have leaflet faces extending across the leaflet width and length that bear against and sweep through the fluid test sample as the agitator vane leaflets are swept about the pivot point within the test chamber. The leaflet faces thereby present high fluid interface profiles to the fluid test sample as the fluid test sample washes against the vane leaflet faces during the sweeping movement of the agitator vane leaflets about the pivot point and through the test sample.

In certain preferred embodiments, the agitator vane leaflets preferably are shaped as paddles or blades that have first and second leaflet faces that are substantially parallel to one another and are substantially parallel to the pivot axis. The leaflet faces can be solid and impermeable by the test sample or can be permeable to the test sample. The agitator vane leaflets can have leaflet edges that are relatively smooth or are notched or roughened.

In a further preferred embodiment, the agitator vane is preferably formed shaped like a propeller wherein the vane leaflets comprise propeller blades each having a blade length, blade width and a blade thickness, and the propeller blades present blade faces that are obliquely angled to the pivot axis.

In still further preferred embodiments, the agitator vane leaflets are each preferably a U-shaped channel extending away from the agitator pivot element.

In yet another preferred embodiment, the agitator vane leaflets are each preferably tubular extending away from the agitator pivot element.

The agitator vane is preferably ferromagnetic, and the sweeping movement of the agitator vane about the pivot point is preferably effected by a sweeping magnetic field that captures and sweeps a ferromagnetic agitator vane leaflet about the pivot point. The sweeping magnetic field is preferably formed by a plurality of electromagnets disposed in a test instrument in relation to a test cartridge receptacle shaped to receive the test cartridge. Electrical sweeping signals are applied to the electromagnets to generate the sweeping magnetic field that effects the sweeping movement. The magnetic field strength is sufficient to impart sweeping movement of the agitator vane when resistance is low in the absence of coagulation of the test sample and is insufficient to overcome resistance to the agitator vane movement that develops with coagulation of the test sample.

During a coagulation time test, a sweeping magnetic field can be generated that effects continuous rotation of the agitator vane through 360° revolutions at a predetermined revolution per minute about the pivot point (when the pivot point is disposed in the center of a cylindrical test chamber). In one preferred method, the sweeping movement comprises alternating clockwise and counter-clockwise sweeps of the agitator vane from a neutral position through predetermined arcs of less than 360° in response to a sweeping signal applied to the electromagnet(s) at a predetermined sweep rate.

In either case, at least one agitator vane sensor is disposed in operative relation to at least one agitator vane and provides an agitator sensor output signal upon each sweep of the agitator vane past the agitator sensor. The agitator sensor output signal waveform varies in signal parameters, e.g., signal amplitude and cycle length, correlated in time to the applied sweeping signal during the coagulation time test. Preferably, the output signal waveform is sampled, digitized and stored as a reference or template waveform during a template establishing time period. Subsequently generated agitator sensor output signals are continually sampled, digitized, and compared to the template waveform. Coagulation is declared when the waveform fails to substantially match the template waveform while the sweeping signal continues to be applied to the electromagnets. A test failure or maximum clotting time is declared if the waveform of the subsequently generated agitator sensor output signal continues to substantially match the template waveform over a predetermined maximum time window following commencement of the coagulation time test.

In a preferred embodiment combining both vane movements and wherein the test chamber is cylindrical, a sweeping signal is generated that effects continuous rotation of the agitator vane through 360° at a predetermined revolution per minute in an initial mixing phase in order to mix the test sample with a reagent, if present. A test phase commences upon completion of the initial mixing phase, wherein the sweeping movement comprises alternating clockwise and counter-clockwise sweeps of the agitator vane from a neutral position through predetermined arcs of less than 360° in response to a sweeping signal applied to the electromagnets at a predetermined sweep rate. The coagulation time is measured either from the commencement of the mixing phase or the test phase until the resistance to sweeping movement is detected. A test failure is declared if the amplitude of the sensor output signal does not vary during the initial mixing phase, and no template waveform can be determined.

In preferred embodiments, at least two test chambers are included in each test cartridge, and redundant tests are performed simultaneously in a test instrument to provide increased accuracy. Other embodiments of the test cartridge may include additional test chambers to increase redundancy or to perform differing tests on the same test sample simultaneously or sequentially.

The test sample may be first mixed with the reagent before deposit in the test chamber, or may contact the reagent coating on the surfaces of an filling channel extending between the blood receptacle and the test chamber. Additionally or alternatively, the test sample may be mixed with a reagent disposed in the test chamber. For example, the agitator vane or surfaces of the test chamber may be coated with the reagent. Or, a discrete element that is coated with or comprises a reagent is disposed in the test chamber. A plurality of test cartridges can be supplied with particular reagents and identified by color or indicia for conducting specific tests of test samples. In a multi-chamber test cartridge, certain of the test chambers may be devoid of any reagent and other test chambers may include a reagent or differing concentrations of reagents.

Moreover, the agitator vane can be surface etched to increase surface area and to enhance surface roughness that tends to cause fibrin to develop in blood test samples. The surface roughness may activate the coagulation of the sample in place of or in addition to a reagent.

Advantageously, the agitator vane is actively swept through the test sample in response to the generated magnetic fields and does not depend on the force of gravity to passively move the agitator vane through the test sample. The continuous, active control of movement of the agitator vane reduces errors introduced with passive control in prior art systems that rely upon gravity.

In addition, the active driving force may be applied to induce the agitator vane to rotate again after the reduction or cessation of movement of the agitator vane is detected to track the continued formation of the clot and the effect of the fibrinolytic process (the breakdown of the clot). The agitator vane may begin to move again due to the applied active driving force as fibrinolysis occurs to weaken the coagulation forces resisting agitator vane movement. The mechanical integrity of the clot over a longer period of time can be assessed, particularly to identify coagulopathic characteristics of the blood test sample.

The agitator vane sensor continuously monitors agitator vane movement thereby capturing any change in movement as soon as the change occurs. In this way, there is no lag time between a change in agitator vane movement and detection of the change.

The present invention is useful for providing information concerning the discrete events that may accompany the coagulation, clotting or lytic process (e.g., clot formation, clot retraction, or clot lysis), as well as provide insight into the overall event. The present invention may be useful in distinguishing between platelet-rich and platelet-poor plasma depending on the clotting profile of the sample. The present invention may also provide information useful to physicians developing a prognosis for patients following cardiopulmonary bypass surgery to avoid or mitigate post-operative bleeding.

This summary of the invention has been presented here simply to point out some of the ways that the invention overcomes difficulties presented in the prior art and to distinguish the invention from the prior art and is not intended to operate in any manner as a limitation on the interpretation of claims that are presented initially in the patent application and that are ultimately granted.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein:

FIG. 7 is an enlarged perspective view of the agitators employed in the test cartridge of FIGS. 2-6;

FIGS. 8-12 are top views of an agitator employed in the test cartridge of FIGS. 1-6 schematically depicting electromagnetic field poles energized by phased sweeping signals for rotating the agitator vane leaflets about the pivot point and the location of an agitator vane sensor disposed to detect to the motion of the agitator vane leaflets;

FIG. 14 is a flowchart illustrating the steps of operation of the system of FIG. 1 employing a test cartridge of FIGS. 1-6;

FIG. 17 is an exploded view of a modified test cartridge of the present invention employing a first variation of the second embodiment of the agitator;

DETAILED DESCRIPTION OF THE PREFERRED EMBODIMENTS OF THE INVENTION

In the following detailed description, references are made to illustrative embodiments of methods and apparatus for carrying out the invention. It is understood that other embodiments can be utilized without departing from the scope of the invention. Preferred methods and apparatus are described for performing blood coagulation tests of the type described above.

Figure 1:
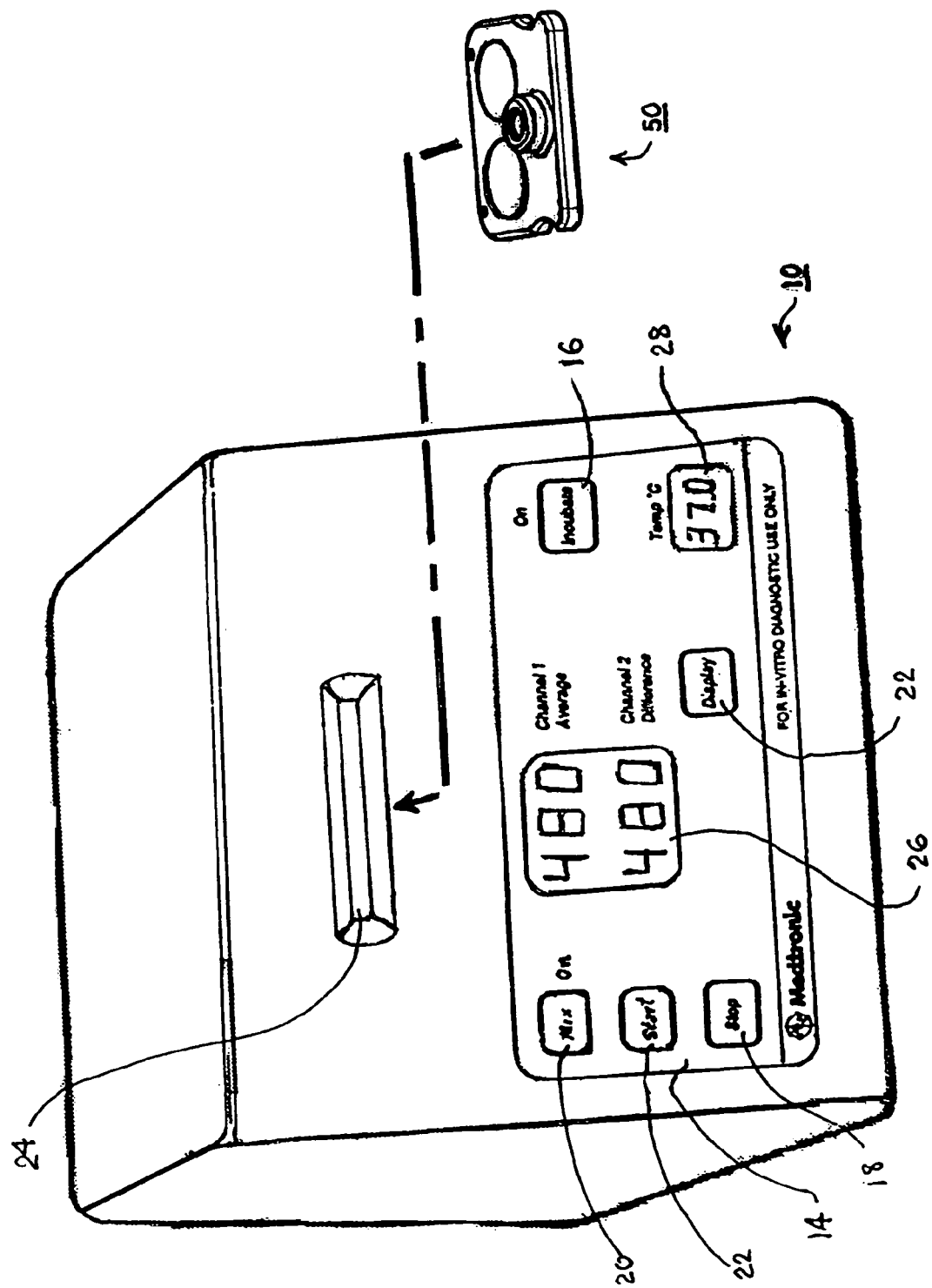
FIG. 1 is a perspective view of a test instrument for receiving a test cartridge and for performing tests on test samples deposited in test chambers of the test cartridge, particularly to determine a blood coagulation time.
Figure 2:
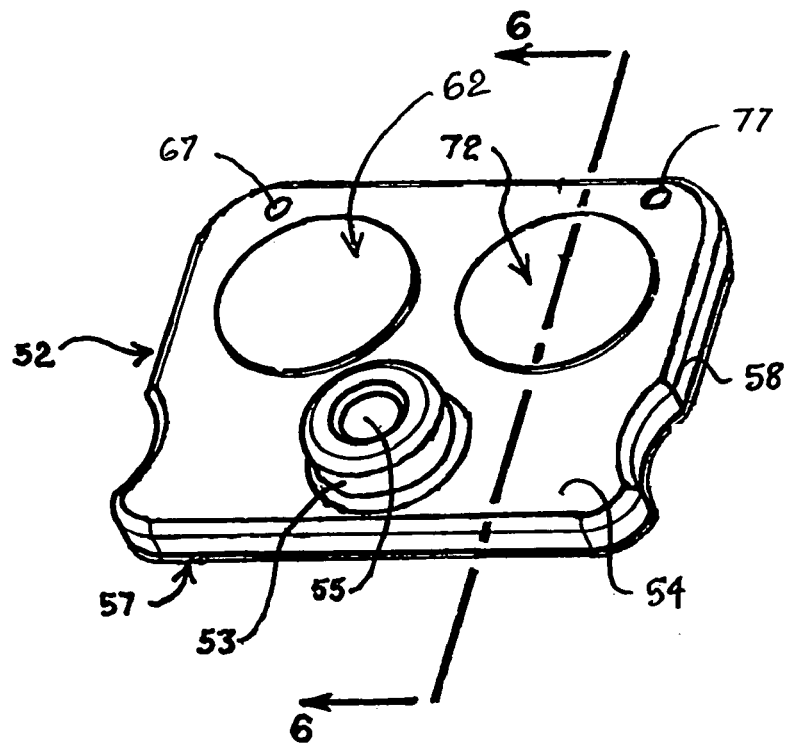
FIG. 2 is a perspective view of one embodiment of a prismatic blood coagulation test cartridge of the present invention having two test chambers.
Figure 3:
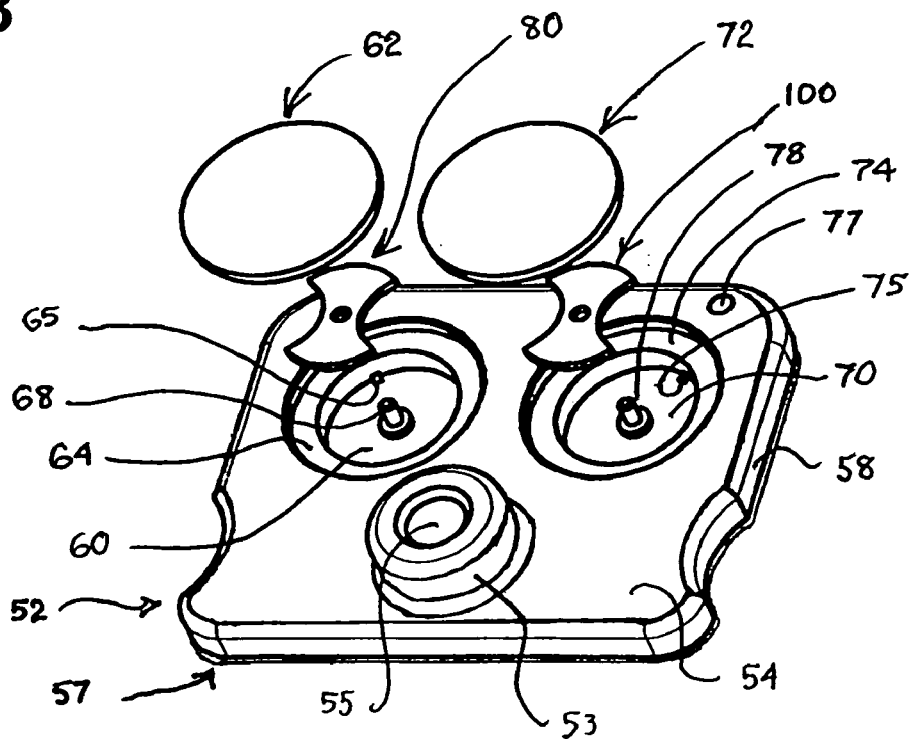
FIG. 3 is an exploded perspective view of the components of the test cartridge of FIG. 2 including the agitators fitted into the test chambers.

FIG. 1 is perspective view of the simplified automatic coagulation time test instrument 10 that can advantageously be used in the practice of the present invention. The test instrument 10 is portable and is operated by battery power or alternatively by power from an AC line. The test instrument 10 has a cartridge receptacle 24 that receives a test cartridge 50 shown in more detail FIGS. 2-6 inserted through the external slot of he cartridge receptacle 24. The test instrument 10 can incubate test samples within the test chambers of the test cartridge 50. The test instrument 10 also conducts coagulation time tests on test samples injected from the same source into two test chambers of the test cartridge 50. The test samples are subjected to the same reagents for conducting redundant coagulation time tests or differing reagents for conducting comparative coagulation time tests. The parallel tests are designated "Channel 1" and "Channel 2" coagulation time tests.

For consistency and accuracy, certain coagulation time tests are conducted on test samples that are "incubated" in the test chambers of the test cartridge 50 by maintaining the test samples at body temperature for a defined incubation time period. It may be necessary to incubate citrated whole blood, plasma, or quality control samples prior to running ACT tests because they may be chilled or at room temperature. Heat is provided also when conducting ACT tests of fresh whole blood employing the test instrument 10 so that the ACT tests are consistently performed at 37° C. (body temperature) rather than at blood test sample temperatures that are elevated or depressed from 37° C. Blood test samples withdrawn from a patient and immediately injected into the test cartridge before the sample has cooled may not need an incubation period and may only need to be maintained at 37° C.

Thus, a heating block (not shown) is incorporated in the test instrument 10 in relation to the cartridge receptacle 24. Preferably the heating block is continuously powered when the test instrument 10 is powered in order to maintain a constant temperature, which is nominally body temperature or 37° C., to a test cartridge 50 inserted into the cartridge receptacle 24. The heating block may be mounted to be manually moved into operative relation with the cartridge receptacle 24 to apply heat to a test cartridge 50 inserted into operative heating relation to the cartridge receptacle 24 or away from cartridge receptacle 24 in the manner of the heating block of the MEDTRONIC® ACT II automated coagulation timer sold by Medtronic, Inc. An Incubate switch 16 is located on the front panel 14 that can be depressed to time out incubation for a predetermined incubation time. An amber, backlit, indicator designated "On" is illuminated when the Incubate switch 16 is activated, and the numerical temperature display 28 displays the temperature of the heating block, which is normally 37° C., incubation temperature.

The front panel 14 also supports a Mix switch 20 and a Start switch 22. The clinician activates the Mix switch 20 when an initial mixing phase is to be included in the coagulation time test. A further amber, backlit, indicator designated "On" is illuminated when the Mix switch 20 is activated. The Start switch 22 is depressed by the clinician to commence a coagulation time test with or without a mixing phase. Additional switches and indicators may be provided on front panel 14 to conduct additional tests or additional analysis beyond determination of the coagulation time of the test sample or test samples.

An LCD screen 26 and four amber, backlit indicators positioned alongside upper and lower display lines of the LCD screen 26 are also supported by the front panel 14. The upper and lower display lines of LCD screen 26 display Channel 1 and Channel 2 incubation or coagulation times. The elapsed or remaining incubation times are displayed for the Channel 1 and Channel 2 test samples when incubation is taking place. The elapsed Channel 1 and Channel 2 coagulation test times are displayed for the Channel 1 and Channel 2 test samples as the coagulation times are being timed out. The final Channel 1 and Channel 2 coagulation test times are then displayed for the Channel 1 and Channel 2 test samples when coagulation is detected.

In addition, the "Average" and "Difference" values of the final Channel 1 and Channel 2 coagulation test times are displayed as the Display Switch 22 is successively depressed. The "Average" and "Difference" can only be displayed by depressing push button display switch 22 upon determination and display of the separate final "Channel 1" and "Channel 2" coagulation times for the two test samples. In each case, the corresponding indicators are backlit to identify the displayed data.

It should be noted that the test instrument operating algorithm could also calculate and display the percent difference between the Channel 1 and Channel 2 coagulation times on the LCD screen 26. A percentage difference greater than a certain threshold (12% in the case of the ACT test) indicates that the coagulation time measurements are "out of tolerance" and that the test should be repeated with a new test sample.

In addition, the upper and lower display lines of LCD screen 26 display Channel 1 and Channel 2 test failure alarms if the coagulation times are too short. For example, a test failure is declared if a coagulation sensor detects coagulation during an initial mixing phase or otherwise too early in the testing phase of one or both of the Channel 1 and Channel 2 coagulation tests.

The front panel 14 also supports a Stop switch 18 that can be depressed by the clinician to terminate either of the incubation phase or the coagulation time test that is in progress. The incubation or coagulation test times that are displayed in display 26 when the Stop switch 18 is depressed are frozen and the displayed times flash.

The elapsed coagulation test times between 6 and 100 seconds are displayed in 1/10 second resolution if the coagulation tests are conducted following incubation of the test samples in the test chambers of the test cartridge 20. Any coagulation test times exceeding 100 seconds are displayed in whole seconds because the 1/10 resolution after 100 seconds is not deemed critical. The 1/10 second resolution is important if a PT test is being performed because PT test times are typically short.

The sensors and circuitry of the test instrument 10 conduct the coagulation time tests on the blood samples in the test chambers of the two test chambers of the test cartridge 50 inserted into the cartridge receptacle 24 in a manner described further below.

A first embodiment of a test cartridge 50 used with the test instrument depicted in FIG. 1 in accordance with the method of FIG. 14 is depicted in FIGS. 2-9. The test cartridge 50 is formed of a cartridge housing 52 and other components described further below. The cartridge housing 52 has a substantially prismatic shape with upper and lower major sides 54 and 56 and a minor cartridge edge or sidewall 58 extending between the upper and lower major sides 54 and 56 and maintaining the upper and lower major sides 54 and 56 in substantially parallel relation. Finger grip indentations are formed in the minor cartridge sidewall 58 to facilitate holding the test cartridge 50 upright, filling test chambers with the test sample, inserting and removing the cartridge housing 52 into and from the instrument cartridge receptacle 24.

The cartridge housing 52 is formed of a transparent and relatively rigid thermoplastic material having one or more, in this case two, cylindrical test chambers 60 and 70 formed extending from the upper major side 54 toward the lower major side 56. A cartridge port 53 extends upward from the upper major side 54, and a port receptacle 55 is sized to receive a test sample dispenser, e.g., a pipette or a hypodermic needle. Filling channels or capillaries 61 and 71 are machined or molded into the lower major side 56 extending from the port receptacle 55 to the test chambers 60 and 70, respectively. Air vent channels or capillaries 65 and 75 are also machined or molded into the lower major side 56 extending from the test chambers 60 and 70, respectively, to air vents 67 and 77, respectively.

A sealing sheet 57 is applied against the lower major side 56 in order to close the filling capillaries 61 and 71 and the air vent capillaries 65 and 75. The sealing sheet is preferably formed of Mylar® plastic sheet or polyester film, e.g., ARcare® 1 mil or 2 mil polyester film available from Adhesives Research, Inc., of Glen Rock, Pa. The ARcare® polyester film is coated on one side with AS-110 acrylic non-migratory inert adhesive that is applied against the lower major side 56 and does not impede capillary flow or contaminate the test sample.

Each air vent 67, 77 may be filled with a vent/fluid seal plug (not shown) that allows air to escape therethrough while blocking flow of liquids therethrough as disclosed in the above-referenced '209 and '286 patents, for example. Suitable vent/fluid seal plugs made of hydrophobic acrylic copolymer on a non-woven support or gas permeable films are available from PALL Life Sciences Division, Ann Arbor, Mich., of Pall Corporation. Alternatively, a gas permeable film or expanded PTFE fabric layer, e.g., a GORE-TEX® laminate filter available from W. L. Gore & Associates, Inc. may be applied over the upper major surface 54 to extend over and close each air vent 67, 77.

The closed test chambers 60, 70 of the test cartridge 50 enclosing the test samples protects against exposure to the blood sample, thereby reducing biohazard risks. The test sample volume is determined by the volume of the test chambers 60, 70 and is not dependent upon operator skill to fill the test chamber 60, 70 to a precise volume. The venting channels and hydrophobic materials allow venting of air from the test chamber 60, 70 during filling to enable filling with a precise test volume and eliminates air bubbles that could alter test results.

Annular seats 64 and 74 in the upper major surface 54 extend around the openings of the test chambers 60 and 70, respectively. Circular chamber caps 62 and 72 formed of a transparent and relatively rigid thermoplastic material are sized in diameter and thickness to fit against annular seats 64 and 74 surrounding the cylindrical test chambers 60 and 70. The peripheral edges of the chamber caps 62 and 72 are either adhered with adhesive or thermally bonded by use of ultrasonic welding techniques to the respective annular seats 64 and 74 to provide a liquid tight seal of the respective cylindrical test chambers 60 and 70. Each test chamber 60 and 70 is therefore substantially cylindrical having a test chamber height between the upper and lower major sides 54 and 56 when the circular chamber caps 62 and 72 are adhered against annular seats 64 and 74 and a test chamber radius measured from the chamber pivot element disposed substantially in the center of the cylindrical test chamber 60 and 70.

The cylindrical test chambers 60 and 70 further include chamber pivot elements 68 and 78, respectively, e.g., the depicted upwardly extending pins or axles that are centrally or axially disposed within the cylindrical test chambers 60 and 70, respectively, and extend upward from the lower major side 56. Free end portions of the chamber pivot elements 68 and 78 are reduced in diameter to an axle diameter. The lower or inner sides or the circular chamber caps 62 and 72 are formed with downwardly extending chamber pivot cups 66 and 76 that are axially aligned with the centers of the circular chamber caps 62 and 72. The free ends of the reduced diameter axles of the chamber pivot elements 68 and 78 fit into the downwardly extending chamber pivot cups 66 and 76, respectively, when the circular chamber caps are fitted into and adhered to the annular seats 64 and 74, respectively.

It will be understood that the arrangement of the chamber pivot element 68, 78 with the chamber pivot cup 66, 76 can be reversed so that the chamber pivot element 68, 78 extends downward from the respective chamber cap 62, 72, and the chamber pivot cup 66, 76 is formed extending upward into the cylindrical test chamber 60, 70 from the second major side 56. In either case, the reduced axle diameters of the chamber pivot elements 68 and 78 provide pivot points of the test chambers 60 and 70 that are intermediate the upper and lower major sides 54 and 56.

In the illustrated embodiments, agitators 80 and 100 are supported by the chamber pivot elements 68 and 78, respectively, within the respective cylindrical test chambers 60 and 70, particularly at the reduced axle diameters of the chamber pivot elements 68 and 78 intermediate the upper and lower major sides 54 and 56. Agitators 80 and 100 comprise agitator pivot elements 88 and 108, respectively, that are engaged by the respective chamber pivot element 68 and 78. In the depicted embodiment, the agitator pivot elements 88 and 108 comprise holes or bores sized in bore diameter to the reduced axle diameters to receive the reduced diameter portions of the upwardly extending pins or axles of the respective chamber pivot elements 68 and 78. In this way, the agitators 80 and 100 are supported at the pivot points of the respective test chambers 60 and 70 intermediate and spaced from the upper and lower major sides 54 and 56.

It will also be understood that the agitator pivot elements 88 and 108 of agitators 80 and 100 could comprise an axle or pin extending upward to fit into the downwardly extending chamber pivot cups 66 and 76 and downward to fit into similar pivot cups extending upwardly from the lower major side 54.

Figure 4:
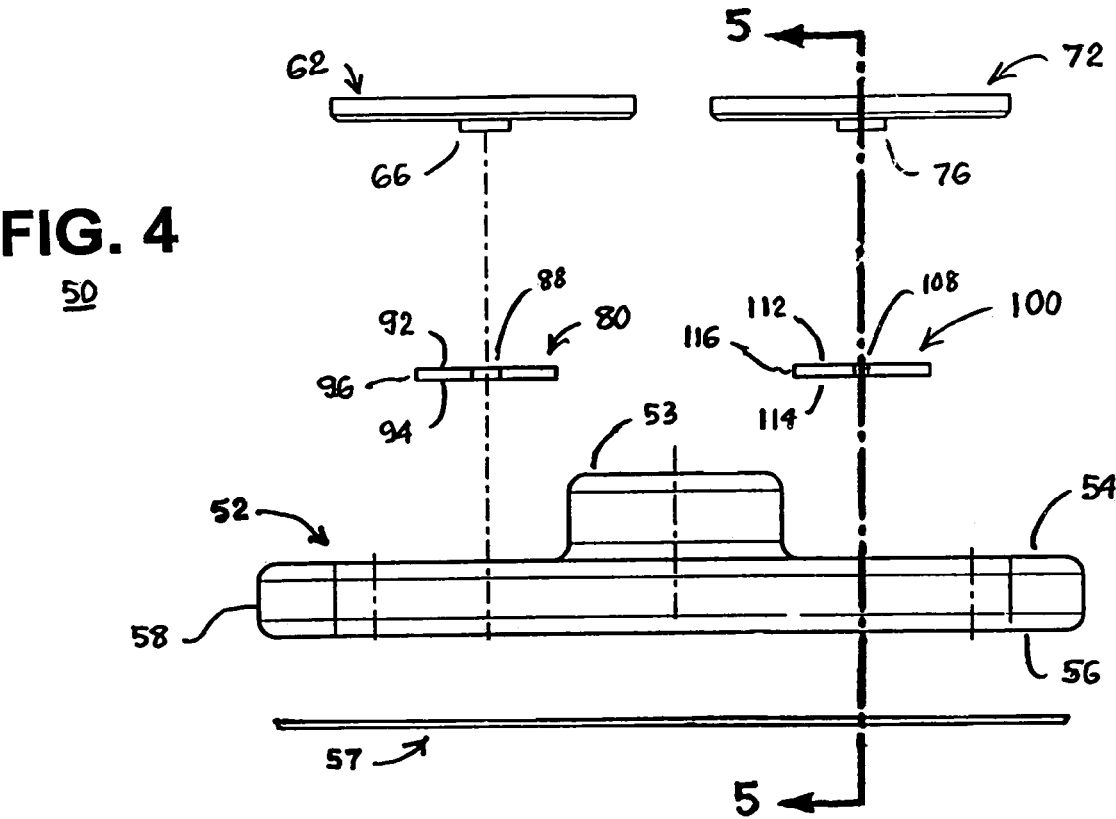
FIG. 4 is an exploded side view of the components of the test cartridge of FIGS. 2 and 3.
Figure 5:
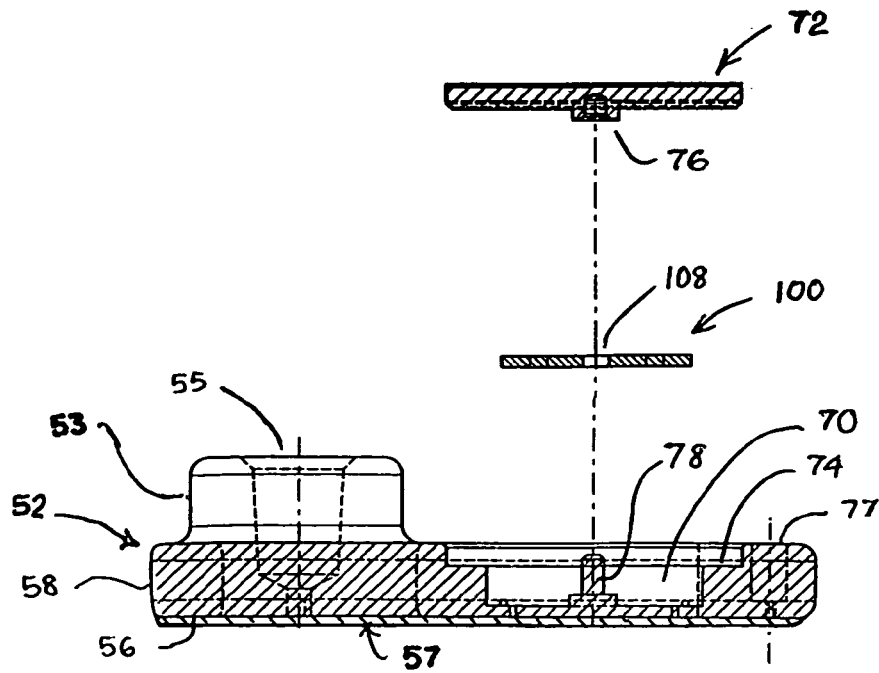
FIG. 5 is a side cross-section view taken along lines 5-5 of FIG. 4.

As called out in FIGS. 4 and 7, the agitators 80 and 100 further comprise an agitator vane formed of agitator vane leaflets 82, 84 and 102, 104, respectively, extending away from agitator pivot elements 88 and 108, respectively, across the radius of the respective test chambers 60 and 70 toward the sidewalls thereof. The agitator vane leaflets 82, 84 and 102, 104 are supported intermediate the first and second major cartridge sides 54 and 56 by the engagement of the respective agitator pivot elements 88 and 108 with the respective chamber pivot elements 68 and 78.

The agitator vane leaflets 82 and 84 of agitator 80 extend away from the agitator pivot element 88 in opposite directions in substantially a common plane with first and second cut-outs or gaps 86 and 90 separating the agitator vane leaflets 82 and 84, whereby the agitator 80 has the appearance of a bowtie. Each agitator vane leaflet 82 and 84 has common upper and lower major surfaces 92 and 94 that are substantially parallel and joined at a vane leaflet edge or sidewall 96 as shown in FIG. 4.

Similarly, the agitator vane leaflets 102 and 104 of agitator 100 extend away from the agitator pivot element 108 in opposite directions in substantially a common plane with first and second cut-outs or gaps 106 and 110 separating the agitator vane leaflets 102 and 104, whereby the agitator 100 has the appearance of a bowtie. Each agitator vane leaflet 102 and 104 has common upper and lower major surfaces 112 and 114 that are substantially parallel and are joined at a vane leaflet edge or sidewall 116 as shown in FIG. 4.

Figure 6:
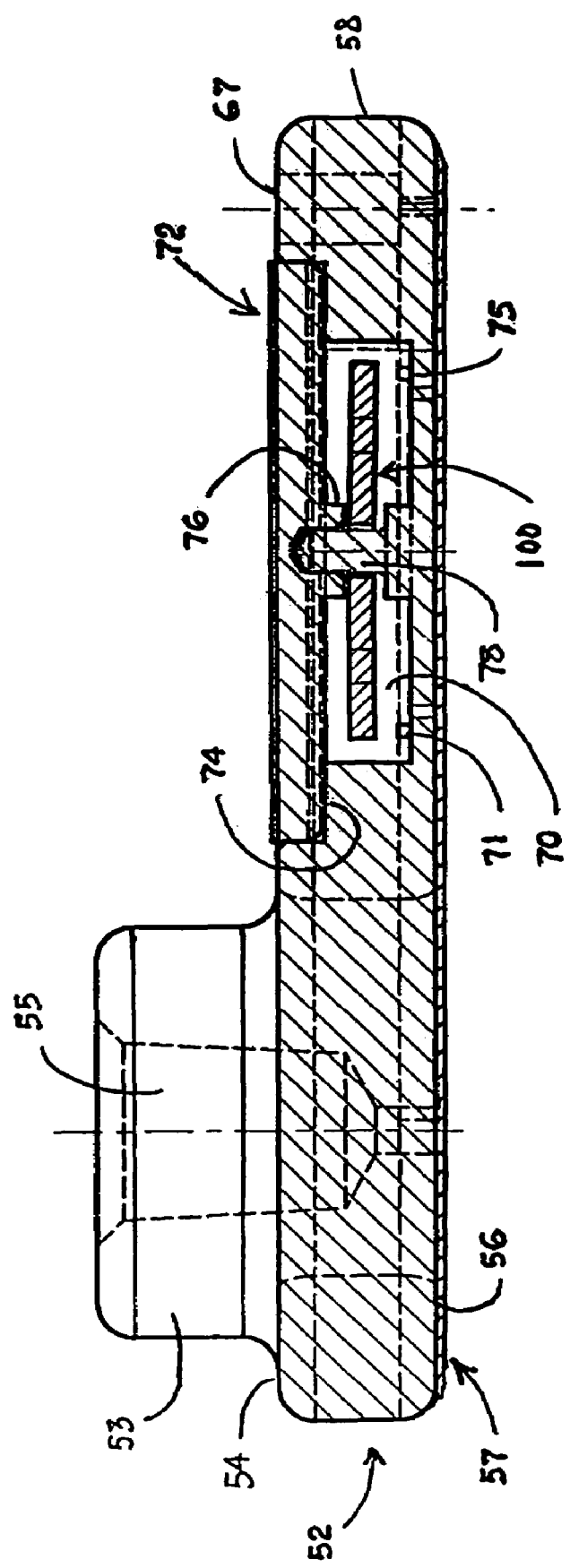
FIG. 6 is a side cross-section view taken along lines 6-6 of FIG. 2.

As shown in FIG. 6, the agitator 100 is supported within test chamber 70 at the pivot point comprising the agitator pivot element 108 and the chamber pivot element 78 to extend substantially parallel with and between the upper and lower major sides 54 and 56. The agitator vane leaflets 102 and 104 preferably each extend from the agitator pivot element 108 substantially across the test chamber radius. The agitator 80 is supported in test chamber 60 in the same orientation to the upper and lower major sides 54 and 56 of the test cartridge housing 52.

A reagent can be deposited in the blood receptacle 55 and/or on surfaces of the filling capillaries 61 and 71 and/or the test chambers 60 and 70, and/or the agitators 80 and 100. A separate element that is formed of or coated with a reagent can alternatively or additionally be placed in the test chambers 60 and 70, e.g., in the shape of a washer placed against the base of the test chambers 60 and 70 below the respective agitators 80 and 100.

A suitable reagent is selected to react with the blood sample to facilitate performance of a test on the blood sample determining test sample coagulation times, e.g., one of TT, PT, aPTT, and ACT, for example. The reagent is selected from coagulants or activating agents including calcium, kaolin, celite, ellagic acid, glass particles, thrombin, thromboplastin or other activating agents or from heparin neutralizing or deactivating agents including heparinase or protamine. One test chamber 60 could contain an activating agent, and the other test chamber 70 could be devoid of an activating agent or contain a neutralizing agent in order to perform comparative coagulation time tests.

Moreover, the agitator vane leaflets 82, 84 and 102, 104 can be surface etched to increase surface area and to enhance surface roughness that tends to cause fibrin to develop in blood test samples as the vane leaflets 82, 84 and 102, 104 are moved through the blood test samples in the respective test chambers 60 and 70.

The test chamber 60, 70 may also contain reagents to counteract any anticoagulants present in the blood sample. During interventional procedures, heparin may be administered to mitigate coagulation induced by the procedure, in which case protamine in the test chamber 60, 70 could counteract heparin and return the blood sample to a baseline condition. One test chamber 60 could contain protamine, and the other test chamber 70 could be devoid of protamine to perform comparative coagulation time tests.

In accordance with one aspect of the present invention, the agitators 80 and 100 are rotated or swept about the respective pivot points in the respective test chambers 60 and 70 to contact the test sample, particularly a blood test sample, therein. The agitator vane leaflets 82, 84 and 102, 104 move freely through the blood test sample until coagulation impedes free movement. Resistance to agitator movement impedes and signifies coagulation of the test sample. The reduction of movement of the agitator vane leaflets 82, 84 and 102, 104 is detected, and coagulation times are determined for each blood sample. The elapsed time measured from starting the sweeping movement and the detection of resistance constitutes a coagulation time.

In one preferred method, the agitator vane leaflets 82, 84 and 102, 104 are continually swept about the pivot points through 360° revolutions at a predetermined revolution per minute in an initial mixing phase in order to mix the test sample with a reagent, if present. A test phase commences upon completion of the initial mixing phase, wherein the sweeping movement becomes oscillatory and comprises alternating clockwise and counter-clockwise sweeps of the agitator vane leaflets 82, 84 and 102, 104 from a neutral position back and forth through predetermined arcs of less than 360°. The alternating clockwise and counter-clockwise sweeps of the agitator vane leaflets 82, 84 and 102, 104 from a neutral angular position are through predetermined arcs of less than 360°, e.g., 45°, 90°, or 180° or between 45° and 90° or between 90° and 180°. The coagulation time is measured either from the commencement of the mixing phase or the test phase until the resistance to sweeping movement is detected.

The resistance caused by the formation of clots or other increase in viscosity halts or slows agitator vane movement, and the slowing or absence of sweeping movement is preferably detected by one or more agitator vane sensor and movement detection circuitry coupled thereto. The agitator vane leaflet sensor may comprise one of a proximity sensor, inductive sensor, magnetic sensor, metal sensor, and optical sensor disposed at a sensor location with respect to the test chamber.

The sweeping movement of the agitator vane leaflets 82, 84 and 102, 104 can be effected in many ways. The agitators 80 and 100 are preferably ferromagnetic, formed of stainless steel, for example, but are not magnetized. Sweeping magnetic fields are preferably generated that capture the ferromagnetic agitators 80 and 100 and sweep the agitator vane leaflets 82, 84 and 102, 104, respectively, about a pivot point PP, through the angular positions depicted in FIGS. 8-12. One of the agitator vane leaflets 82, 84 and 102, 104 is marked for convenience along one outer edge as shown in FIGS. 8-12 to depict the sweeping movement of each agitator 80, 100 about the pivot point PP through 360°.

The sweeping magnetic field that effects continuous rotation of each agitator 80, 100 about a pivot point PP through 360° revolutions is preferably created by application of four electrical sweeping signals $SS_1$, $SS_2$, $SS_3$, and $SS_4$ to four respective miniaturized electromagnet 42, 44, 46, 48. The four respective miniaturized electromagnet 42, 44, 46, 48 are supported within the test instrument 10 arrayed alongside and around each test chamber 60, 70 when the test cartridge 50 is seated in the aperture 24. It will be understood that the electromagnets 42, 44, 46, 48 are schematically depicted in FIGS. 8-12, and that the actual orientation of the physical embodiments may differ from the depiction. For example, two sets of the physical electromagnets 42, 44, 46, 48 may be disposed in two arrays along one side of the aperture 24 or distributed for convenience of spacing along both sides of the aperture 24. The electromagnets 42, 44, 46, 48 may also comprise electromagnet pairs placed above and below the aperture 24 receiving the test cartridge 50. Each pair of electromagnets operating in tandem helps balance the forces applied to the agitator leaflets or the agitators 80 and 100 and the sweeping movement about the pivot points within the respective test chambers 60 and 70.

The test cartridge housing 52 may also be shaped with indentations to fit against and dispose the sets of electromagnets 42, 44, 46, 48 in close relation to each test chamber and the vane leaflets therein so that the primary magnetic flux lines are aligned in the same plane as the vane leaflets to balance electromagnetic forces applied to the vane leaflets.

The sweeping signals $SS_1$, $SS_2$, $SS_3$, and $SS_4$ may take any convenient alternating waveform, e.g., triangular with a peak as depicted, truncated triangular, sinusoidal or square. The rise and fall times of each triangular wave excursion may be the same in slope or may differ. Each positive excursion of the sweeping signals $SS_1$, $SS_2$, $SS_3$, and $SS_4$ causes a magnetic field of a North or South polarity, and each negative excursion of the sweeping signals $SS_1$, $SS_2$, $SS_3$, and $SS_4$ causes a magnetic field of the opposite South or North polarity. The sweeping signals $SS_1$, $SS_2$, $SS_3$, and $SS_4$ are 90° out of phase with respect to one another. Thus, North and South polarity magnetic fields are sequentially generated around the circumference of the test chambers 60 and 70 that pass through the agitator vane leaflets 82, 84 and 102, 104 and effect rotation of each agitator 80, 90 about its pivot point PP in a clockwise or counterclockwise (as depicted) direction.

Generally speaking, each agitator 80, 100 is rotated about each pivot point PP like the rotor of a brush-less electric motor as the rising and falling alternating magnetic fields attract and repel the agitator vane leaflets agitator vane leaflets 82, 84 and 102, 104.

The sweeping magnetic field that effects back and forth pivotal movement of the agitators 80 and 100 about each pivot point PP through an arc less than 360°, e.g., about a 180° arc, is preferably created by application of two of the depicted alternating sweeping signals $SS_1$, and $SS_3$, or $SS_2$ and $SS_4$ to the respective miniaturized electromagnets 42 and 46 or 44 and 48. A fixed amplitude, positive polarity, biasing signal is applied to one of the remaining pair of electromagnets, and a fixed amplitude, negative polarity, biasing signal is applied to the other one of the remaining pair of electromagnets. The relative magnitudes of the sweeping signals as compared to those of the fixed biasing signals determine the angular displacement of the vane resulting in an arc of movement between 0° and 180°.

The magnetic field strength is sufficient to selectively impart sweeping movement of the agitators 80 and 100 through full 360° continuous revolutions and in the back and forth rotation through about a 180° arc when resistance is low in the absence of rising viscosity in the test sample, e.g., clotting or coagulation of a blood sample. But, the magnetic field strength is not sufficient to overcome resistance to sweeping movement that develops when such a viscosity increase occurs.

As shown in FIGS. 8-12 (and in FIG. 15), agitator vane sensors 40 and 40' are supported by the test instrument 10 along one side of aperture 24 in relation to each test chamber of a test cartridge inserted into aperture 24. For example, when the test cartridge 50 is seated in the aperture 24, each test chamber 60, 70 is disposed alongside a set of agitator vane sensors 40 and 40'. As shown, one agitator vane sensor 40 is disposed radially aligned between the pivot point PP and the electromagnet 48, and the second agitator vane sensor 40' is disposed between adjacent electromagnets 46 and 48. In practice, either one or both of the agitator vane sensors 40, 40' can be provided for each test chamber 60, 70.

The agitator vane sensors 40 and 40' can comprise one of a proximity sensor, inductive sensor, magnetic sensor, metal sensor, and optical sensor disposed at an agitator sensor location with respect to each test chamber 60, 70. The agitator vane sensor 40, 40' for each test chamber 60, 70 provides an agitator sensor output signal AS OUT upon each sweep of each agitator vane leaflet past the agitator vane sensor 40, 40'. The AS OUT signals of the agitator vane sensors 40 and 40' can be processed electrically for redundancy. Moreover, the AS OUT signals of the agitator vane sensors 40 and 40' can be processed electrically to obtain additional information relating to the motion profile of the vane leaflets moving through the test sample. Changes in acceleration of the vane leaflets in response to the applied magnetic fields can be discerned from changes in the phase relationship between the AS OUT signals generated by the agitator vane sensors 40 and 40'. The changes in acceleration could potentially indicate clotting characteristics ("micro" clots, more localized or generalized clots, etc.) of the test sample prior to the actual clotting event and indicate further clotting events during the lysis stage after clotting.

Figure 13:
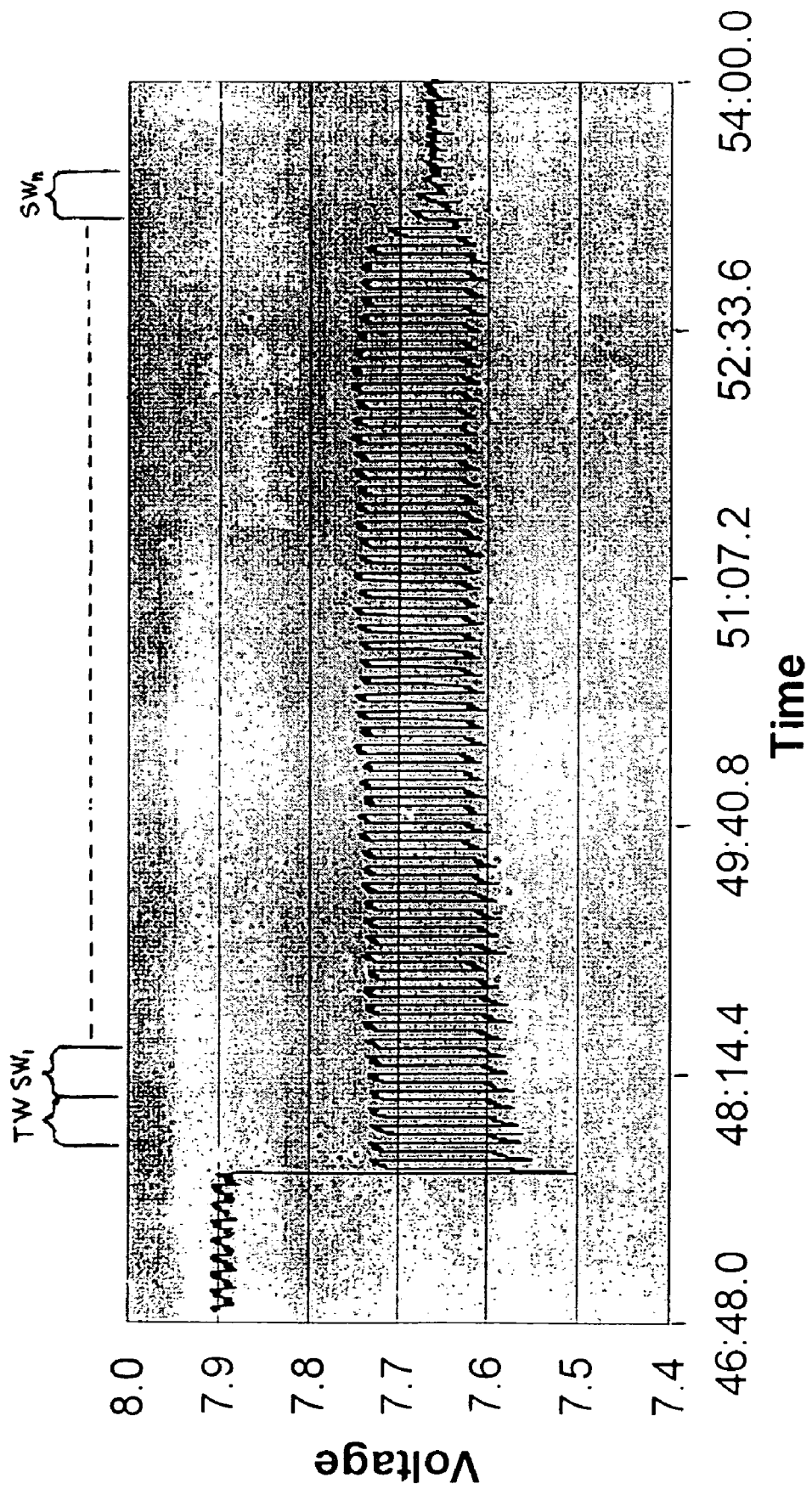
FIG. 13 is a diagram of agitator sensor output signals observed in a coagulation time test employing the test cartridge of FIGS. 1-6 during rotation as depicted in FIGS. 8-12 and upon cessation of rotation.

For convenience, it will be assumed in the following discussion that only one AS sensor 40 is employed. Preferably, the agitator vane sensor 40 develops an AS OUT signal exhibiting cyclic oscillations in amplitude over time as depicted in FIG. 13, for example, as a function of changes in inductance as the agitator leaflets sweep past the agitator vane sensor 40. The depicted AS OUT signal has a period or cycle correlated in time to the applied sweeping signal and varies in amplitude from a biasing voltage as the agitator 80, 100 moves freely through the test sample during the initial phase of a coagulation time test (assuming no failure). The peak positive and negative amplitude excursions of the AS OUT signal are relatively large in absolute amplitude with respect to the baseline 7.9 volts, and the signal cycle length is regular since the moving agitator vane tracks the changes in the applied magnetic field.

An initial AS OUT signal sample window is sampled, digitized and temporarily stored to be employed as a AS OUT signal template window TW. As time passes, subsequent AS OUT signal sample windows $SW_1$-$SW_n$ are successively defined, sampled, digitized, and compared to the template window TW employing any simple template matching algorithm to provide a $\Delta$ AS value. The $\Delta$ AS value remains low as long as the current AS OUT signal sample window SW closely matches the AS OUT signal template window TW, e.g., in comparing TW with $SW_1$. The $\Delta$ AS value increases when the current AS OUT signal sample window SW no longer closely matches the AS OUT signal template window TW, e.g., in comparing TW with $SW_n$. Coagulation is declared and the final coagulation test time is displayed when the $\Delta$ AS value increases and exceeds a $\Delta$ AS threshold "T" while the sweeping signals continue to be applied to the electromagnets 42, 44, 46 and 48 or pairs thereof. It will be understood that other detection criteria and algorithms or comparator circuitry could be employed to process the AS OUT signal and detect slowing or cessation of movement of the agitator vane.

A test failure is declared if the $\Delta$ AS value increases and exceeds the $\Delta$ AS threshold T during the mixing phase or during a "too early" initial portion of the test phase. Similarly, a "maximum test time exceeded" test failure is declared if the elapsed coagulation test time exceeds a predetermined failure time.

It will be understood that tracing of the oscillating AS OUT signal generated by each agitator vane sensor 40 as illustrated, for example, in FIG. 13, can also or alternatively be displayed in the Channel 1 and Channel 2 display lines on LCD screen 26 of test instrument 10. If such displays are provided, the clinician may observe the changes that occur in the oscillating AS OUT signal as fibrin builds up around the agitator vane leaflets, and vane leaflet motion changes.

The test cartridge 50 can be employed in the system 10 depicted in FIG. 1 operating in accordance with the steps of the method depicted in FIG. 14. Certain of the method steps are practiced by an algorithm and/or circuitry of a preferably microcomputer-based controller of the test instrument 10.

Turning to FIG. 14, a test sample, e.g. a blood test sample, is drawn in step S100 in any conventional manner into a sample source and is optionally pre-mixed with a reagent. In step S102, a syringe or a pipette filled with the test sample is directed over the cartridge port 53 to deposit the test sample into the receiving chamber 55, and the test sample is conveyed into the test chambers 60 and 70. The test cartridge 50 is inserted in step S104 into the aperture 24 and may be incubated by the heat block therein to body temperature for a preset time period as described above. It will be understood that steps S102 and S104 can be reversed since the test cartridge 50 could be inserted into the aperture 24 with the cartridge port 53 exposed so that the test sample can be deposited into the receiving chamber 55 and passed through the filling channels into the test chambers 60 and 70.

As noted above, a mixing phase can be selected by depressing the Mix switch 20, as determined in step S106, so that the agitators 80 and 100 are rotated continually for a preset time period to sweep around and mix the test samples in the respective test chambers 60 and 70 in step S108. The coagulation test timer is started at the same time in step S108, since coagulation of the test sample commences in the mixing phase. Each agitator sensor 40 is also powered in step S110 to derive the AS OUT signals particularly to ensure that no error condition is present during the mixing phase. The mixing phase, if selected in step S106, ends upon time out of a mixing time as determined in step S108.

When the test phase is commenced in step S110, the agitators 80 and 100 are preferably swept back and forth at a preset rate through an arc of less than about 180° as described above. A AS OUT signal template window is derived in step S112 from the AS OUT signals of each agitator sensor 40 of each channel and temporarily stored in separate memory registers. Current AS OUT signal sample windows are successively selected in step S114 as the AS OUT signals are generated by each agitator sensor 40. The derived current AS OUT signal sample window of each channel is compared to the AS OUT signal template window of that channel employing a template matching algorithm, for example, in step S116 to derive a difference signal $\Delta AS$ for the channel. The difference signal $\Delta AS$ of each channel is compared to a threshold T in step S118.

For each channel, coagulation is declared and the coagulation test time is determined in step S120 when the difference signal $\Delta AS$ of the channel exceeds the threshold T as determined in step S118. The coagulation test time determined in step S120 is temporarily stored and can be immediately displayed in the appropriate "Channel 1" or "Channel 2" display line of the LCD screen 26.

The coagulation time tests are declared completed in step S122 when the coagulation times are determined in step S120 for both blood test samples. Then, it is possible in step S124 to calculate the average and difference values from the at least two determined and temporarily stored coagulation test times for display in the appropriate "Channel 1" or "Channel 2" display line of the LCD screen 26. The Stop switch 18 is depressed, and the test cartridge 50 is then removed from the aperture 24 and suitably disposed of in step S126.

It will be understood that the algorithm of FIG. 14 may be modified to provide that the tracings of the oscillating AS OUT signals generated by each agitator vane sensor 40 are displayed in the Channel 1 and Channel 2 display lines on LCD screen 26 of test instrument 10 in addition to the displayed coagulation test times. If such displays are provided, the clinician may observe the changes that occur in the oscillating AS OUT signal as fibrin builds up around the agitator vane leaflets and later due to the fibrinolytic process. The agitator vane may begin to move again in response to the applied magnetic fields as fibrinolysis occurs to weaken the coagulation forces resisting agitator vane movement. The mechanical integrity of the clot over a longer period of time can be assessed, particularly to identify coagulopathic characteristics of the blood test sample before the clinician depresses the Stop switch 18 in step S126.

Figure 27:
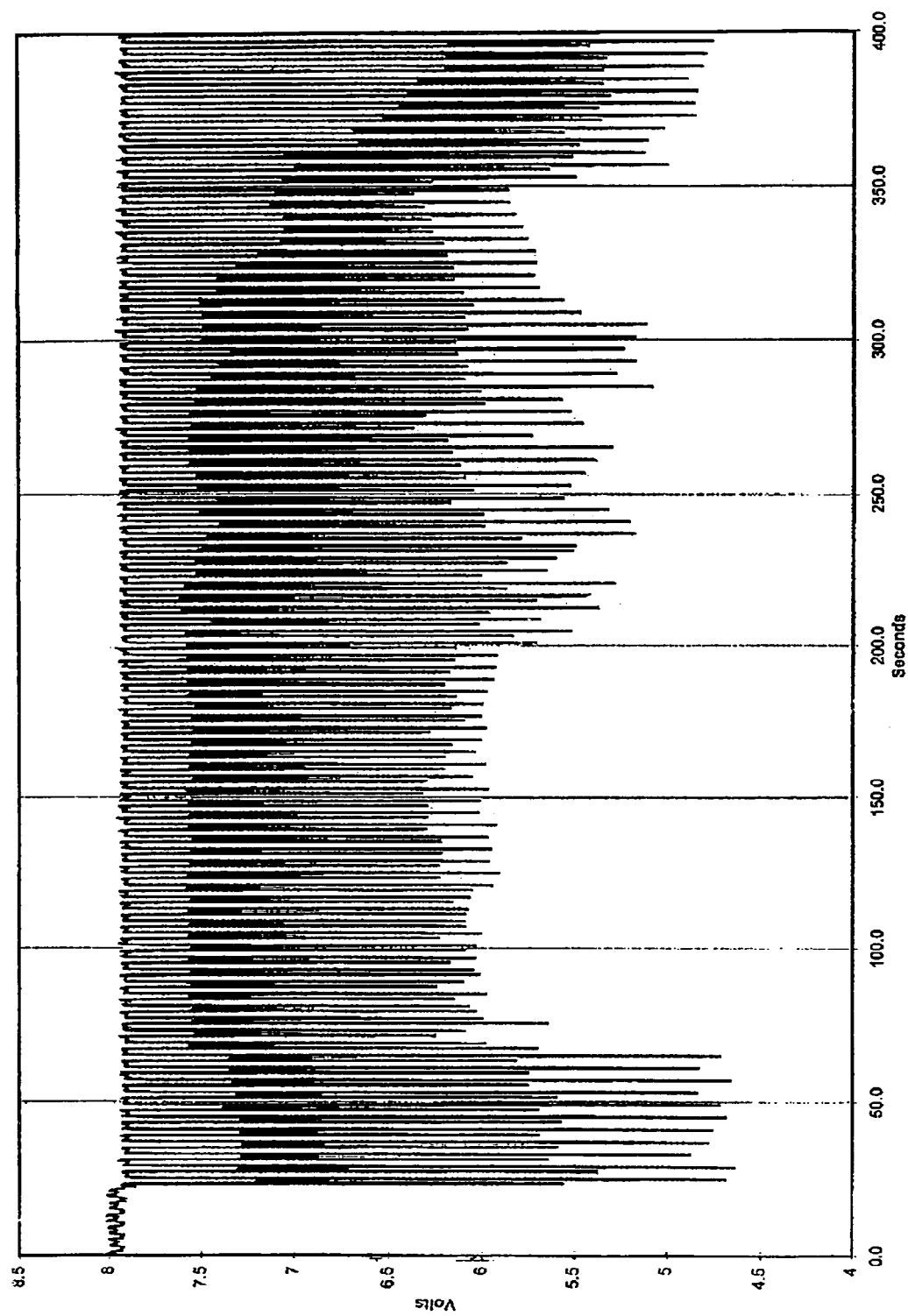
FIG. 27 is a diagram of agitator sensor output signals observed in a coagulation time test showing the effects of coagulation and subsequent fibrinolysis upon movement of an agitator vane through the test sample.

An example of such behavior is depicted in the tracing of AS OUT signals over a prolonged time period appearing in FIG. 27 that could be displayed on the LCD screen 26. After an initial 25 second delay, the AS OUT signal varies between the baseline 7.9 volts and about 4.6 volts until about 75 seconds have elapsed. Then, the AS OUT signal variation diminishes to between the baseline 7.9 volts and about 6.0 volts due to a reduction in vane movement as movement is resisted by coagulation of the test sample. Coagulation would be declared at about 80 seconds employing the techniques described above. Then, the AS OUT signal varies between the baseline 7.9 volts and about 5.5 seconds at about 220 seconds as the agitator vane begins to move more freely in response to the applied magnetic fields and as fibrinolysis occurs to weaken the coagulation forces resisting agitator vane movement. At about 350 seconds, coagulation and fibrinolysis re-balance is restored, as evidenced by the resumption of variation of the AS OUT signal between the baseline 7.9 volts and about 4.6 volts. Thus, the clinician is afforded a more complete understanding of the coagulopathic characteristics of the blood test sample. This long term behavior of the blood test sample depicted, for example in the tracing of FIG. 27 is not possible to observe with prior art coagulation timers that depend upon devices that passively fall under the force of gravity through the test sample.

In the depicted preferred embodiments described above, two test chambers 60 and 70 are included in each test cartridge 50, and the instrument 10 is configured and programmed to simultaneously perform redundant coagulation time tests to provide increased accuracy or distinct coagulation time tests of test samples exposed to differing reagents to derive distinct comparative coagulation times. Other embodiments of the test cartridge may include additional test chambers to increase redundancy or to perform differing tests on the same test sample simultaneously or sequentially, and the test instrument may be modified to perform the additional tests.

For example, six test chambers can be included in each test cartridge in an array that is adapted to be inserted into the aperture of a test instrument having six sets of internally disposed agitator rotating electromagnet sets and agitator sensors operable substantially as described herein. In such a six-chamber test cartridge, three redundant tests can be conducted employing differing reagents. For example, two test chambers can be devoid of any reagent, two test chambers can include a small quantity of heparin, and two further test chambers can include a larger quantity of heparin. The three duplicate ACT test results provide heparin dose response (HDR) data points that can be plotted to determine a patient's individual heparin response. The patient's heparin needs during bypass can be extrapolated based on this response curve.

The above described agitators 80 and 100 can be characterized as "flat" agitators because the agitator sidewalls 96 and 116 are relatively small in surface area compared to the upper and lower major surfaces 92, 94 and 112, 114, respectively. Moreover, the agitator thickness, i.e., the width or height of the sidewalls 96 and 116, is relatively small in relation to the depth or height (hereafter test chamber height) of the test chambers 60 and 70 as shown in FIG. 6. The sidewalls of the flat agitator leaflets 82, 84 and 102, 104 present agitator sweeping face surface areas applied against the test sample that are about less than 40% of the test chamber cross-section areas of the respective test chambers 60 and 70. While excellent coagulation time tests can be performed on blood and biologic test samples, there may be concern that coagulation times are prolonged because the agitator sweeping faces sweeping against less than 50% of the volume of the test samples may tend to cut through developing fibrin strands and clots.

Figure 15:
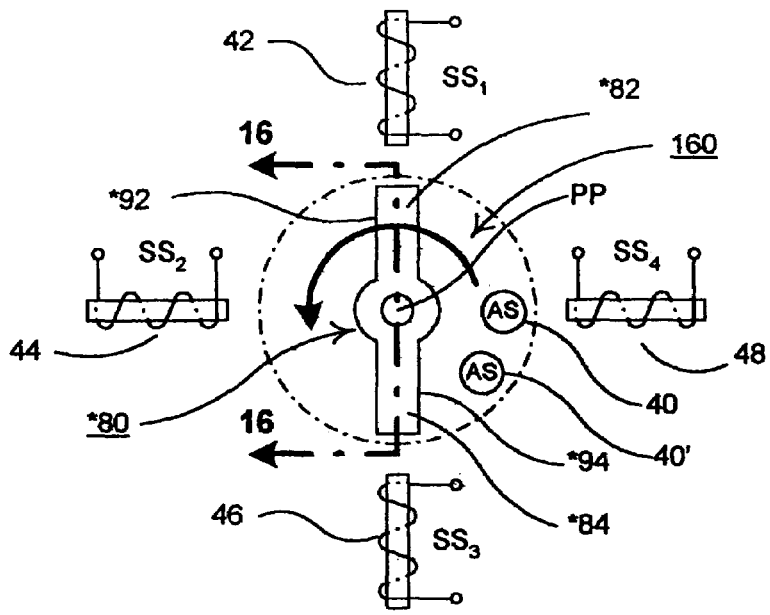
FIG. 15 is a top view of a second embodiment of an agitator employed in a test cartridge of the type depicted in FIGS. 1-6 or FIG. 16 adapted to be swept about the pivot point in relation to an agitator vane sensor as in FIGS. 8-12 by schematically depicted electromagnetic field poles energized by phased sweeping signals that rotate the agitator vane leaflets, wherein the agitator leaflets present enlarged agitator leaflet sweeping faces against the test sample disposed in the test chamber during rotation of the agitator vane leaflets.
Figure 16:
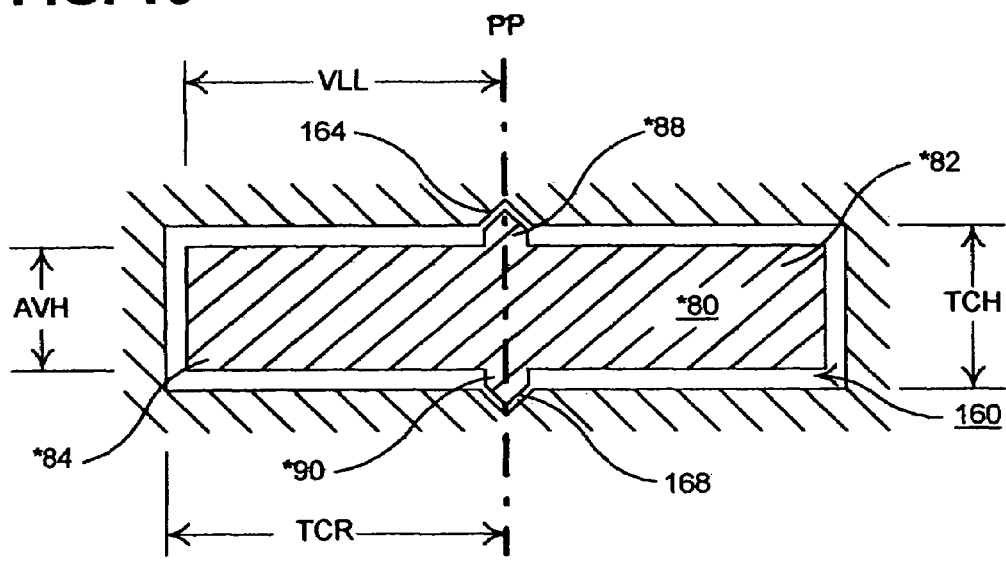
FIG. 16 is a cross-section view of the second embodiment of the agitator in relation to the test chamber of FIG. 15.

In accordance with a further aspect of the present invention, alternative agitators ***80, schematically depicted in FIGS. 15 and 16, have been developed and tested that are shaped to have agitator vane leaflets having agitator sweeping faces that sweep through a higher fraction of the test chamber height during rotation of the agitator vane leaflets. The schematically depicted agitator ***80 comprises first and second agitator vane leaflets ***82 and ***84 extending in opposed directions away from the agitator pivot elements ***88 and ***90. It will be understood that the agitator pivot elements ***88 and ***90 fit within cup-shaped test chamber pivot elements of a test chamber 160 of a modified test cartridge 150, whereby the agitator and test chamber pivot elements together define the test chamber pivot point PP and a pivot point axis PP-PP as shown in FIG. 16. It will also be understood that the alternative pivot point PP and pivot axis provided by the axle and hole structure depicted in the test cartridge 50 in FIGS. 3, 5 and 6 can be substituted for the pivot elements ***88 and ***90 fitting within the cup-shaped test chamber pivot elements.

As shown in FIG. 16, the agitator vane and the vane leaflets ***82 and ***84 have an agitator vane height AVH, and the agitator vane leaflets ***82 and ***84 have a leaflet thickness, and a vane leaflet length VLL measured from the pivot point axis at PP-PP. Each agitator vane leaflet ***82 and ***84 extends from the pivot point PP substantially across the test chamber radius TCR. The agitator vane length AVL is equal to twice the vane leaflet length VLL, and the test chamber diameter TCD is equal to twice the test chamber radius TCR. The agitator vane height AVH is somewhat smaller than the test chamber height TCH, and the leaflet thickness is less than the agitator vane height AVH and the vane leaflet length VLL. The vane leaflet sweeping faces have a surface area defined by AVH×AVL that can be up to about 90% of the test chamber cross-section area defined by TCH×TCD. Stated another way, the agitator vane of agitator ***80 has an agitator vane height AVH extending substantially through the test chamber height TCH and an agitator vane length AVL extending substantially through the test chamber diameter TCD.

The enlarged leaflet sweeping faces ***92 and ***94 present high fluid interface profiles to the fluid test sample as the fluid test sample washes against the leaflet sweeping faces ***92 and ***94 during the sweeping movement of the agitator vane leaflets ***82 and ***84 about the pivot point PP and through the test sample within test chamber 160.

In certain preferred embodiments, the leaflet sweeping faces ***92 and ***94 preferably are shaped as paddles wherein the respective leaflet sweeping faces ***92 and ***94 are substantially parallel to one another and are substantially parallel to the pivot axis as shown in FIGS. 15 and 16. In other embodiments, the leaflet sweeping faces ***92 and ***94 of the agitator vane leaflets ***82 and ***84 are not necessarily parallel to one another, but are symmetric. The agitator embodiments of FIGS. 17-26 are denoted ***80, wherein *** is 1, 2, 3, 4, 5, 6, 7, 8, 9, 10; each such agitator embodiment can be substituted for the flat agitators 80 and 100 of the test cartridge 50** or the modified test cartridge 150 depicted in FIG. 17 (with suitable agitator and test chamber pivot elements).

A first alternative agitator 180 is depicted in FIG. 17 in relation to the modified test cartridge 150 having a single test chamber 160 that is formed in a cartridge housing 152 and enclosed by a circular chamber cap 162. The cartridge housing 152 has a substantially prismatic shape with upper and lower major sides 154 and 156 and a minor cartridge edge or sidewall 158 extending between the upper and lower major sides 154 and 156 and maintaining the upper and lower major sides 154 and 156 in substantially parallel relation. Finger grip indentations can be formed in the minor cartridge sidewall 158 to facilitate holding the test cartridge 150 upright, filling test chambers with the test sample, inserting and removing the cartridge housing 152 into and from the instrument cartridge receptacle 24. A port receptacle 155 into the upper major side 154 is sized to receive a test sample dispenser, e.g., a pipette or a hypodermic needle. A filling channel is machined or molded into the lower major side 156 extending from the port receptacle 155 to the test chamber 160. An air vent channel 165 is also machined or molded into the lower major side 56 extending from the test chamber 160 to an air vent 167 that may be sealed as described above with respect to air vent 167. A sealing sheet can be applied against the lower major side 156 in order to close the filling capillary and the air vent capillary 165. An annular seat 164 in the upper major surface 154 extends around the opening of the test chamber 160. The circular chamber cap 162 is formed of a transparent and relatively rigid thermoplastic material that is are sized in diameter and thickness to fit against and be sealed into annular seat 164 as described above with respect to chamber caps 62 and 72. One cup-shaped test cartridge pivot element 168 is depicted in FIG. 17. The test cartridge 150 may have one or more additional test chamber as described above with respect to the test cartridge 50.

In each of the following described embodiments of the agitator *80, the change in agitator vane movement is detected from the processing of the AS OUT signals developed by the agitator sensor 40 as described above with respect to FIGS. 13 and 14.

The alternative agitator 180 depicted in FIG. 17 comprises agitator vane leaflets 182 and 184 extending away from vane pivot elements 188 and 190 that have respective leaflet sweeping faces 192 and 194. The vane leaflets 182 are shaped so that the respective leaflet sweeping faces 192 and 194 are curved or concave like a scoop along the vane leaflet length VLL from the pivot point PP defined by vane pivot elements 188 and 190 as shown in FIG. 15. In blood test samples, fibrin strands forming during coagulation are scooped up, slowing rotation or reducing the agitator vane range of motion, and possibly eventually halting the rotation of the agitator 180 about the pivot point PP.

Figure 18:
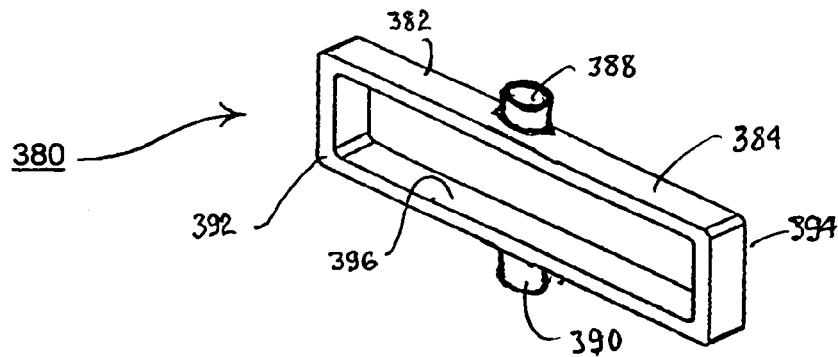

The alternative "window" agitator 380 depicted in FIG. 18 has a rectangular frame 396 defining a window supported by the agitator pivot elements 388 and 390 to provide the opposed vane leaflets 382 and 384. The opposed vane leaflets 382 and 384 have vane leaflet sweeping faces 392 and 394 that sweep through the test sample in test chamber 160 when the agitator vane leaflets 382 and 384 are rotated about the pivot point PP in the counterclockwise direction as shown in FIG. 15. In blood test samples, fibrin strands forming during coagulation catch on the rectangular frame 396 tending to fill the window and slowing rotation or reducing the agitator vane range of motion, and possibly eventually halting the rotation of the window agitator 380 about the pivot point PP.

Figure 19:
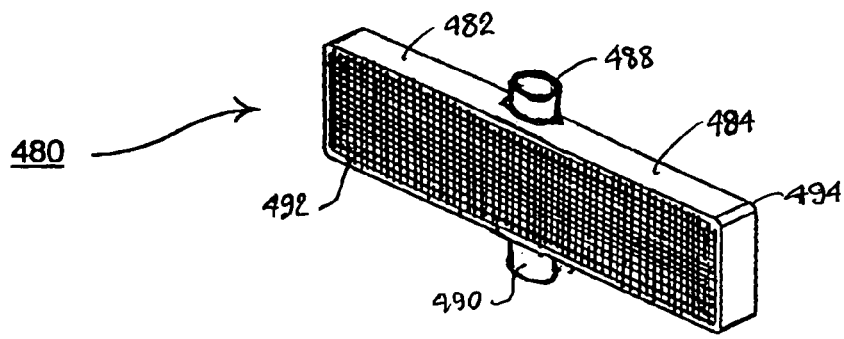

The alternative "mesh" agitator 480 depicted in FIG. 19 has porous mesh layers 492 and 494 supported by or adhered to the sides of the hollow rectangular frame forming the opposed vane leaflets 482 and 484 supported by the agitator pivot elements 488 and 490. The porous mesh layers 492 and 494 can comprise wire or fabric mesh layers or a single porous mesh layer fitted within the rectangular frame. The porous mesh layers 492 and 494 constitute the vane leaflet sweeping faces that sweep through the test sample in test chamber 160 when the agitator vane leaflets 482 and 484 are rotated about the pivot point PP in the counterclockwise direction as shown in FIG. 15. In blood test samples, fibrin strands forming during coagulation catch on the mesh layers 492 and 494, slowing rotation or reducing the agitator vane range of motion, and possibly eventually halting the rotation of the mesh agitator 480 about the pivot point PP.

Figure 20:
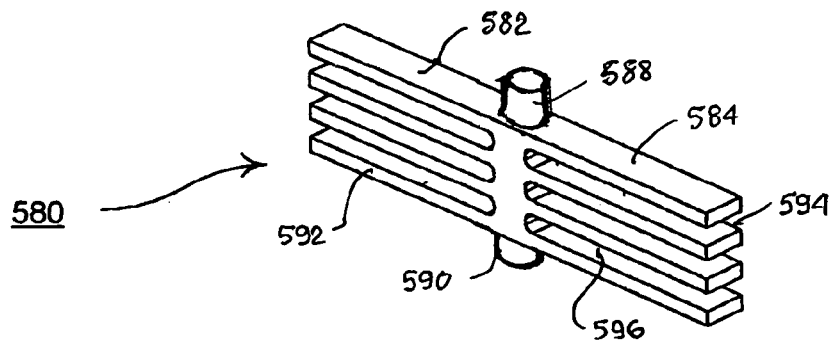

The opposed vane leaflets 582 and 584 of the "comb" agitator 580 supported by the agitator pivot elements 588 and 590 are slotted with slots 596 as depicted in FIG. 20 to form a plurality of comb tines that sweep through the test sample. The opposed vane leaflets 582 and 584 have vane leaflet sweeping faces 592 and 594, respectively, that sweep through the test sample in test chamber 160 when the agitator vane leaflets 582 and 584 are rotated about the pivot point PP in the counterclockwise direction as shown in FIG. 15. In blood test samples, fibrin strands forming during coagulation are raked out of the test sample by the tines and accumulate in the slots 596, slowing rotation or reducing the agitator vane range of motion, and possibly eventually halting the rotation of the comb agitator 580 about the pivot point PP.

Figure 21:
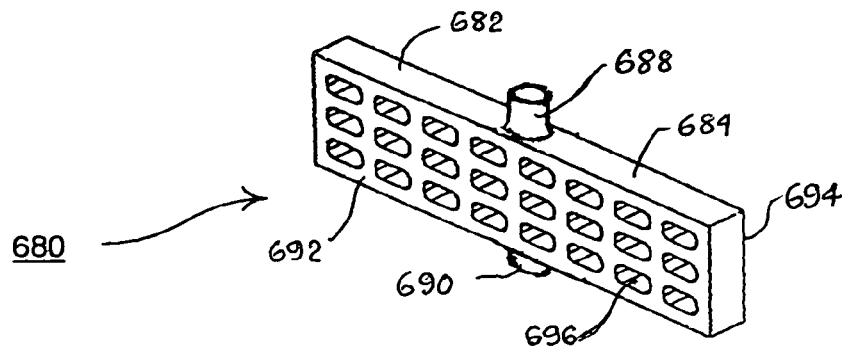

"Sieve" holes 696 are formed as depicted in FIG. 21 extending through the opposed vane leaflets 682 and 684 of the sieve agitator 680 supported by the agitator pivot elements 688 and 690 that sweep through the test sample. The opposed vane leaflets 682 and 684 have vane leaflet sweeping faces 692 and 694, respectively, that sweep through the test sample in test chamber 160 when the agitator vane leaflets 682 and 684 are rotated about the pivot point PP in the counterclockwise direction as shown in FIG. 15. In blood test samples, fibrin strands forming during coagulation catch and accumulate in the sieve holes 696, slowing rotation or reducing the agitator vane range of motion, and possibly eventually halting the rotation of the sieve agitator 680 about the pivot point PP.

Figure 22:
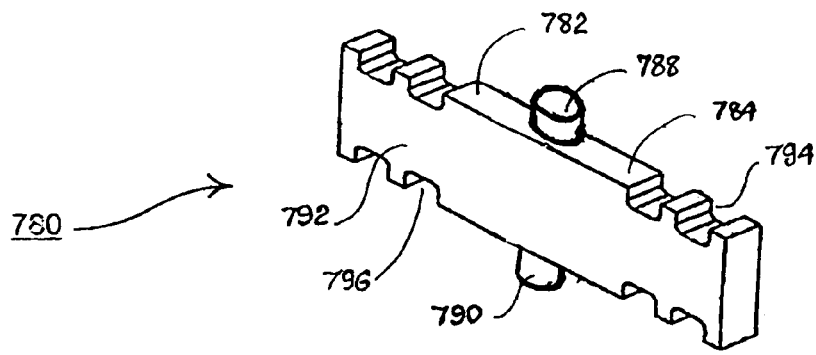

Notches 796 are formed as depicted in FIG. 22 along the upper and lower edges of the opposed vane leaflets 782 and 784 of the "notched bar" agitator 780 supported by the agitator pivot elements 788 and 790 that sweep through the test sample. The opposed vane leaflets 782 and 784 have vane leaflet sweeping faces 792 and 794, respectively, that sweep through the test sample in test chamber 160 when the agitator vane leaflets 782 and 784 are rotated about the pivot point PP in the counterclockwise direction as shown in FIG. 15. In blood test samples, fibrin strands forming during coagulation catch and accumulate in the notches 796, slowing rotation or reducing the agitator vane range of motion, and possibly eventually halting the rotation of the notched bar agitator 780 about the pivot point PP.

Figure 23:
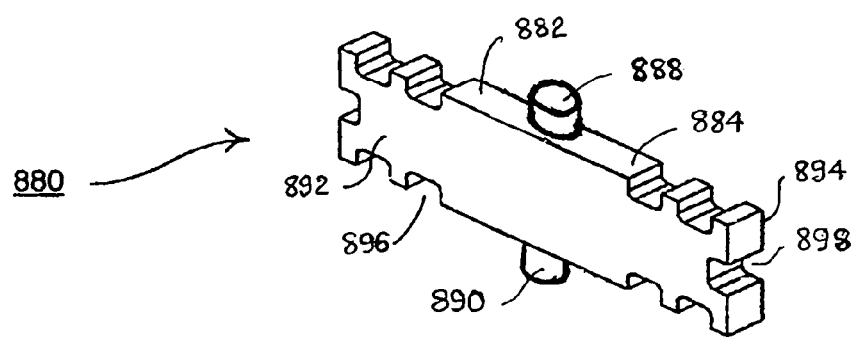

Notches 896 and 898 are formed as depicted in FIG. 23 along the vane leaflet ends as well as the upper and lower edges of the opposed vane leaflets 882 and 884 of the "notched end" agitator 880 supported by the agitator pivot elements 888 and 890 that sweep through the test sample. The opposed vane leaflets 882 and 884 have vane leaflet sweeping faces 892 and 894, respectively, that sweep through the test sample in test chamber 160 when the agitator vane leaflets 882 and 884 are rotated about the pivot point PP in the counterclockwise direction as shown in FIG. 15. In blood test samples, fibrin strands forming during coagulation catch and accumulate in the notches 896 and 898, slowing rotation or reducing the agitator vane range of motion, and possibly eventually halting the rotation of the notched agitator 880 about the pivot point PP.

Figure 24:
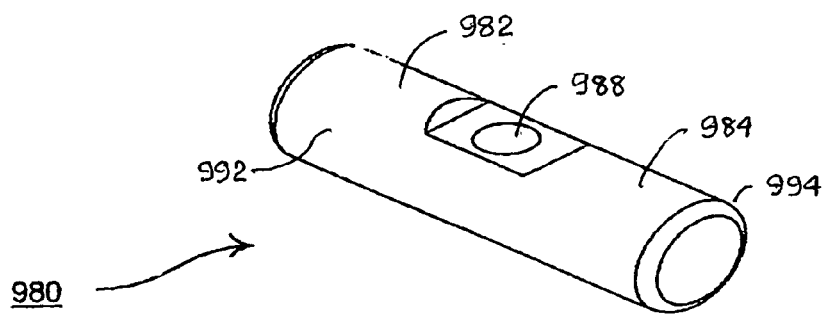

A "tube" agitator 980 is depicted in FIG. 24 where the agitator vane comprises an elongated tube having a tube diameter corresponding to agitator height AVH of FIG. 16 and forming the agitator vane leaflets 982 and 984 extending away from the agitator pivot element 988. The agitator pivot element 988 in this example comprises an axle bore extending transverse to the tube axis adapted to receive an axle, centrally or axially disposed within the cylindrical test chamber 160, e.g., the axle 78 of the test chamber 70 as depicted in FIG. 6 and described above. The opposed vane leaflets 982 and 984 have vane leaflet sweeping faces 992 and 994, respectively, that present symmetric convex curved leaflet sweeping faces against the test sample disposed in the test chamber during rotation of the agitator vane leaflets 982 and 984. The vane leaflet sweeping faces 992 and 994 sweep through the test sample in test chamber 160 when the agitator vane leaflets 982 and 984 are rotated about the pivot point PP in the counterclockwise direction as shown in FIG. 15. In blood test samples, fibrin strands forming during coagulation catch and accumulate around the convex vane leaflet sweeping faces 992 and 994, slowing rotation or reducing the agitator vane range of motion, and possibly eventually halting the rotation of the tube agitator 880 about the pivot point PP.

Figure 25:
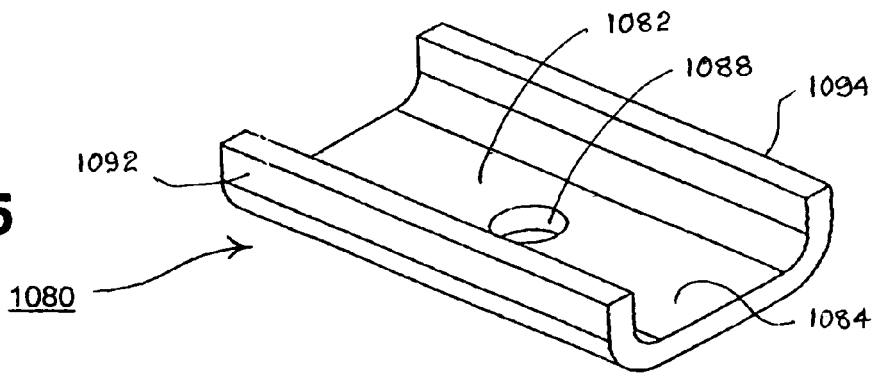

A "U-shape" agitator 1080 is depicted in FIG. 25 where the agitator vane comprises a U-shaped channel having a channel side height corresponding to agitator height AVH of FIG. 16 and forming the agitator vane leaflets 1082 and 1084 extending away from the agitator pivot element 1088. The elongated U-shaped channel extends between opposed channel ends and an agitator pivot element 1088 is formed between the opposed channel ends. The agitator pivot element 1088 in this example comprises an axle bore extending transverse to the tube axis adapted to receive an axle, centrally or axially disposed within the cylindrical test chamber 160, e.g., the axle 78 of the test chamber 70 as depicted in FIG. 6 and described above. The opposed vane leaflets 1082 and 1084 have vane leaflet sweeping faces 1092 and 1094, respectively, that sweep through the test sample in test chamber 160 when the agitator vane leaflets 1082 and 1084 are rotated about the pivot point PP in the counterclockwise direction as shown in FIG. 15. In blood test samples, fibrin strands forming during coagulation catch and accumulate on the vane leaflet sweeping faces 1092 and 1094, slowing rotation or reducing the agitator vane range of motion, and possibly eventually halting the rotation of the U-shape agitator 1080 about the pivot point PP.

Figure 26:
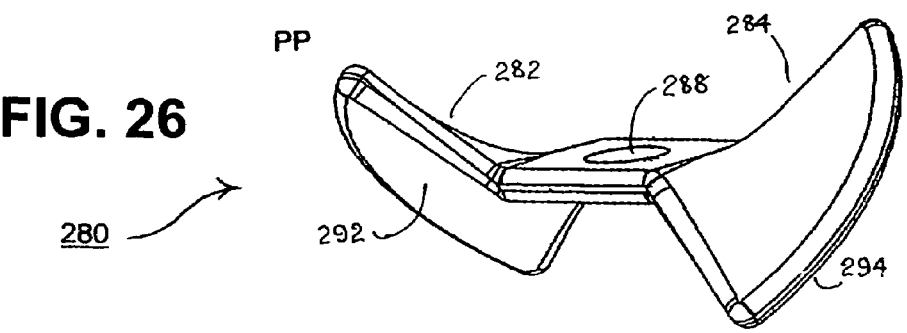
FIGS. 18-26 are perspective views of alternative preferred agitator embodiments incorporating dimensional features of the agitator of FIG. 16 usable in the test cartridge embodiment of FIGS. 1-6 or FIG. 16.

A "propeller" agitator 280 is depicted in FIG. 26 wherein the agitator vane comprises a propeller having opposed propeller blades each having a propeller blade height corresponding to agitator height AVH of FIG. 16. The agitator pivot element 288 in this example comprises an axle bore extending transverse to the tube axis adapted to receive an axle, centrally or axially disposed within the cylindrical test chamber 160, e.g., the axle 78 of the test chamber 70 as depicted in FIG. 6 and described above. The agitator vane leaflets 282 and 284 extending away from the agitator pivot element 288 are shaped like symmetric propeller blades having complementary pitches with respect to the pivot axis. The propeller blade shaped vane leaflets 282 and 284 therefore have vane leaflet sweeping faces 292 and 294, respectively, that sweep through the test sample in test chamber 160 when the agitator vane leaflets 282 and 284 are rotated about the pivot point PP in the counterclockwise direction as shown in FIG. 15. In blood test samples, fibrin strands forming during coagulation catch and accumulate on the vane leaflet sweeping faces 1092 and 1094, slowing rotation or reducing the agitator vane range of motion, and possibly eventually halting the rotation of the propeller agitator 280 about the pivot point PP.

Thus, the leaflet sweeping faces can be solid and impermeable to the test sample or can be permeable to the test sample. The agitator vane leaflets can have leaflet sweeping faces and edges that are relatively smooth or are notched or roughened. The leaflet sweeping faces may also be coated or roughened to encourage coagulation.

As noted above, the agitator vane sensor continuously monitors agitator vane movement thereby capturing any change in movement as soon as the change occurs. In this way, there is no lag time between a change in agitator vane movement and detection of the change.

All patents and publications referenced herein are hereby incorporated by reference in their entireties.

It will be understood that certain of the above-described structures, functions and operations of the above-described preferred embodiments are not necessary to practice the present invention and are included in the description simply for completeness of an exemplary embodiment or embodiments.

In addition, it will be understood that specifically described structures, functions and operations set forth in the above-referenced patents can be practiced in conjunction with the present invention, but they are not essential to its practice.

It is to be understood, that within the scope of the appended claims, the invention may be practiced otherwise than as specifically described without actually departing from the spirit and scope of the present invention. The disclosed embodiments are presented for purposes of illustration and not limitation, and the present invention is limited only by the claims that follow.

The invention claimed is:

1. A system comprising:
   a test cartridge comprising:
      a cartridge housing having at least one cylindrical test chamber therein into which a test sample is deposited to be tested, the test chamber having a test chamber axis, a test chamber diameter and a test chamber height defining a test chamber volume; and an agitator mounted at a pivot point at the test chamber axis, the agitator having an agitator vane adapted to be swept about the pivot point and through the test sample in the test chamber, the agitator vane having an agitator vane height extending substantially through the test chamber height and an agitator vane length extending substantially through the test chamber diameter; and
   a test instrument comprising:
      an instrument housing including a cartridge receptacle for supporting the test cartridge; sweeping means for sweeping the agitator vane about the pivot point through the test sample in substantially the full test chamber volume; detecting means for detecting a reduction of sweeping movement of the agitator vane; and timing means for timing a coagulation test time elapsed from the commencement of sweeping of the agitator vane until the detection of reduction of the sweeping movement,
   wherein the test cartridge is formed of the cartridge housing and comprises a test chamber pivot element; and the agitator vane comprises an agitator pivot element engaging the test chamber pivot element allowing rotational motion of the agitator vane about a pivot axis at the pivot point, and wherein the agitator vane comprises first and second agitator vane leaflets extending in opposed directions away from the pivot axis through the agitator vane length presenting agitator leaflet sweeping faces bounded by vane leaflet edges against the test sample disposed in the test chamber during rotation of the agitator vane leaflets.

2. The system of claim 1, wherein the agitator vane leaflets are symmetric and shaped in the form of propeller blades and present symmetric, curved propeller sweeping faces against the test sample disposed in the test chamber during rotation of the agitator vane leaflets.

3. The system of claim 1, wherein the agitator vane is tubular and the agitator vane leaflets are symmetric and present symmetric convex curved leaflet sweeping faces against the test sample disposed in the test chamber during rotation of the agitator vane leaflets.

4. The system of claim 1, wherein the agitator vane leaflets are symmetric and present symmetric substantially flat leaflet sweeping faces against the test sample disposed in the test chamber during rotation of the agitator vane leaflets.

5. The system of claim 4, wherein the agitator vane comprises an elongated U-shaped channel extending between opposed channel ends and an agitator pivot element between the opposed channel ends.

6. The system of claim 4, wherein the vane leaflet edges are notched.

7. The system of claim 1, wherein the agitator vane comprises an elongated U-shaped channel extending between opposed channel ends and an agitator pivot element between the opposed channel ends.

8. The system of claim 1, wherein the vane leaflet edges are notched.

9. The system of claim 1, wherein the agitator vane leaflets are symmetric and present symmetric substantially convex leaflet sweeping faces against the test sample disposed in the test chamber during rotation of the agitator vane leaflets.

10. The system of claim 9, wherein the agitator vane comprises an elongated tube extending between opposed tube ends and an agitator pivot element between the opposed tube ends.

11. The system of claim 1, wherein the agitator vane leaflets are symmetric and present symmetric concave curved leaflet sweeping faces against the test sample disposed in the test chamber during rotation of the agitator vane leaflets.

12. The system of claim 1, wherein the agitator vane leaflets are symmetric and present symmetric leaflet sweeping faces having notched leaflet edges against the test sample disposed in the test chamber during rotation of the agitator vane leaflets.

13. The system of claim 1, wherein the agitator vane leaflets are formed by a substantially rectangular frame surrounding a leaflet window, whereby the agitator vane leaflets present leaflet sweeping faces having at least one window against the test sample disposed in the test chamber during rotation of the agitator vane leaflets.

14. The system of claim 13, wherein the frame supports a mesh disposed across the leaflet window.

15. The system of claim 1, wherein the agitator vane leaflets have a plurality of sieve holes extending through the agitator vane leaflets, whereby the agitator vane leaflets present leaflet sweeping faces having a plurality of sieve holes against the test sample disposed in the test chamber during rotation of the agitator vane leaflets.

16. The system of claim 1, wherein the agitator vane leaflets have a plurality of slots extending through the agitator vane leaflets, whereby the agitator vane leaflets present leaflet sweeping faces having a plurality of substantially parallel teeth against the test sample disposed in the test chamber during rotation of the agitator vane leaflets.

17. The system of claim 16, wherein the plurality of substantially parallel teeth of each vane leaflet extend away from the pivot axis.

18. The system of claim 1, wherein a mesh is disposed across the agitator leaflet sweeping faces.

* * * * *